(12) United States Patent
Soma et al.

(10) Patent No.: US 12,144,547 B2
(45) Date of Patent: Nov. 19, 2024

(54) CONTROL DEVICE AND METHOD, AND SURGICAL MICROSCOPE SYSTEM

(71) Applicant: Sony Corporation, Tokyo (JP)

(72) Inventors: Yoshio Soma, Kanagawa (JP); Tomoyuki Ootsuki, Kanagawa (JP); Junichiro Enoki, Kanagawa (JP); Tatsumi Sakaguchi, Kanagawa (JP)

(73) Assignee: Sony Corporation, Tokyo (JP)

(*) Notice: Subject to any disclaimer, the term of this patent is extended or adjusted under 35 U.S.C. 154(b) by 1085 days.

(21) Appl. No.: 16/980,845

(22) PCT Filed: Mar. 8, 2019

(86) PCT No.: PCT/JP2019/009268
§ 371 (c)(1),
(2) Date: Sep. 15, 2020

(87) PCT Pub. No.: WO2019/181554
PCT Pub. Date: Sep. 26, 2019

(65) Prior Publication Data
US 2021/0015362 A1    Jan. 21, 2021

(30) Foreign Application Priority Data

Mar. 22, 2018 (JP) .................. 2018-054229

(51) Int. Cl.
*A61B 3/10* (2006.01)
*A61B 3/00* (2006.01)
(Continued)

(52) U.S. Cl.
CPC .............. *A61B 3/13* (2013.01); *A61B 3/0025* (2013.01); *A61B 3/0058* (2013.01); *A61B 3/102* (2013.01);
(Continued)

(58) Field of Classification Search
CPC ....... A61B 3/13; A61B 3/0025; A61B 3/0058; A61B 3/102; A61B 90/20; A61B 2090/364; A61B 2090/371; G02B 21/0012
(Continued)

(56) References Cited

U.S. PATENT DOCUMENTS

2006/0203330 A1* 9/2006 Moeller ............. G02B 21/0012
359/377
2008/0002151 A1* 1/2008 Hideshima ............. A61B 3/102
351/208
(Continued)

FOREIGN PATENT DOCUMENTS

| JP | 2006-247399 A | 9/2006 |
| JP | 2008-000342 A | 1/2008 |
| JP | 2018-180119 A | 11/2018 |

OTHER PUBLICATIONS

International Search Report and Written Opinion mailed on May 21, 2019 for PCT/JP2019/009268 filed on Mar. 8, 2019, 10 pages including English Translation of the International Search Report.

*Primary Examiner* — Mahidere S Sahle
(74) *Attorney, Agent, or Firm* — XSENSUS LLP

(57) ABSTRACT

The present technology relates to a control device and method that can focus on a desired position of a subject, and a surgical microscope system.

The control device includes: an initial in-focus position detection unit configured to detect a focus position when focusing on a predetermined subject included in an observation image of an eye of a patient that is a surgical operation target as an initial in-focus position; and a calculation unit configured to determine an offset value indicating a distance between a target eye organ that is inside a corneal endothelium of the eye and the initial in-focus position on the basis of information regarding structure of an eyeball, (Continued)

and to calculate an in-focus position that is a focus position focused on the target eye organ on the basis of the offset value and the initial in-focus position. The present technology is applicable to the surgical microscope system.

20 Claims, 12 Drawing Sheets

(51) Int. Cl.
    *A61B 3/13*     (2006.01)
    *A61B 90/00*     (2016.01)
    *A61B 90/20*     (2016.01)
    *G02B 21/00*     (2006.01)

(52) U.S. Cl.
    CPC ......... *A61B 90/20* (2016.02); *A61B 2090/364* (2016.02); *A61B 2090/371* (2016.02); *G02B 21/0012* (2013.01)

(58) Field of Classification Search
    USPC .................. 351/205, 206, 208, 211, 221
    See application file for complete search history.

(56) References Cited

U.S. PATENT DOCUMENTS

| | | | |
|---|---|---|---|
| 2014/0132918 A1* | 5/2014 | Aikawa | A61B 3/14 351/246 |
| 2014/0267675 A1* | 9/2014 | Matsunobu | G02B 7/34 348/80 |
| 2018/0289254 A1* | 10/2018 | Matsunobu | A61B 3/0075 |

* cited by examiner

CONTROL DEVICE AND METHOD, AND SURGICAL MICROSCOPE SYSTEM

CROSS-REFERENCE TO RELATED APPLICATIONS

The present application is based on PCT filing PCT/JP2019/009268, filed Mar. 8, 2019, which claims priority to JP 2018-054229, filed Mar. 22, 2018, the entire contents of each are incorporated herein by reference.

TECHNICAL FIELD

The present technology relates to a control device and method, and a surgical microscope system, and in particular to a control device and method that can focus on a desired position of a subject, and a surgical microscope system.

BACKGROUND ART

For example, in order to perform an accurate and safe surgical operation in an ophthalmic surgical operation under a surgical microscope, it is necessary to adjust the focus position of the microscope appropriately according to a situation during the surgical operation and to always observe with a clear visual field without a blur.

In a surgical microscope equipped with a camera, that is, in a video surgical microscope, complicated focus position alignment can be automated by an autofocus (AF) function using an image.

However, in contrast AF, phase difference AF, and the like, which are widely used in digital cameras and the like, the AF performance largely depends on the texture of a subject, and focusing on an object without an edge is difficult in principle.

Therefore, in an ophthalmic surgical operation, which is mainly targeted for observation and treatment of a transparent body without an edge such as the cornea, the crystalline lens, and the vitreous body, accurate focus position alignment using existing AF technology cannot be expected.

Therefore, a system for focusing on the cornea has been proposed by moving the focus position by a distance based on an average value of the corneal curvature, the corneal shape measured by pattern illumination, and the like after focusing on a virtual image produced by emitting illumination light on the cornea (see, for example, Patent Document 1).

CITATION LIST

Patent Document

Patent Document 1: Japanese Patent Application Laid-Open No. 2017-148361

SUMMARY OF THE INVENTION

Problems to be Solved by the Invention

However, by the method described in Patent Document 1, it is theoretically difficult to align the focus position on the surface of the eye other than the cornea, and this method cannot be applied to a surgical microscope that requires focusing on the crystalline lens, the vitreous body, and the like inside the eyeball according to the type and progress of the surgical operation. Therefore, a technology that allows focusing on a desired position of the subject such as the crystalline lens and the vitreous body is desired.

The present technology has been made in view of such a situation, and makes it possible to focus on a desired position of the subject.

Solutions to Problems

A control device according to a first aspect of the present technology includes: an initial in-focus position detection unit configured to detect a focus position when focusing on a predetermined subject included in an observation image of an eye of a patient that is a surgical operation target as an initial in-focus position; and a calculation unit configured to determine an offset value indicating a distance between a target eye organ that is inside a corneal endothelium of the eye and the initial in-focus position on the basis of information regarding structure of an eyeball, and to calculate an in-focus position that is a focus position focused on the target eye organ on the basis of the offset value and the initial in-focus position.

A control method according to the first aspect of the present technology includes: detecting a focus position when a predetermined subject included in an observation image of an eye of a patient that is a surgical operation target is focused as an initial in-focus position; and determining an offset value indicating a distance between a target eye organ inside a corneal endothelium of the eye and the initial in-focus position on the basis of information regarding structure of an eyeball, and calculating an in-focus position that is a focus position focused on the target eye organ on the basis of the offset value and the initial in-focus position.

According to the first aspect of the present technology, a focus position when a predetermined subject included in an observation image of an eye of a patient that is a surgical operation target is focused is detected as an initial in-focus position; and an offset value indicating a distance between a target eye organ inside a corneal endothelium of the eye and the initial in-focus position on the basis of information regarding structure of an eyeball is determined, and an in-focus position that is a focus position focused on the target eye organ on the basis of the offset value and the initial in-focus position is calculated.

A surgical microscope system according to a second aspect of the present technology is a surgical microscope system corresponding to the control device according to the first aspect of the present technology.

Effects of the Invention

According to the first aspect and the second aspect of the present technology, a desired position of the subject can be focused.

Note that advantageous effects described here are not necessarily restrictive, and any of the effects described in the present disclosure may be applied.

MODE FOR CARRYING OUT THE INVENTION

Embodiments to which the present technology is applied will be described below with reference to the drawings.

First Embodiment

<Configuration Example of Surgical Microscope System>

The present technology allows a surgical microscope system to focus on a desired position in eyeball tissue including a transparent body by using an offset value calculated from general AF technology, information regarding eyeball structure, and the like.

Note that the following describes an example in which a subject that is an observation target is a patient's eye that is a surgical operation target. However, the subject that is an observation target is not limited to the eye, but may be any subject such as, for example, a subject observed with an endoscope or a subject including a transparent body. In particular, the present technology is useful in a case where a subject including a transparent body is focused.

Figure 1:
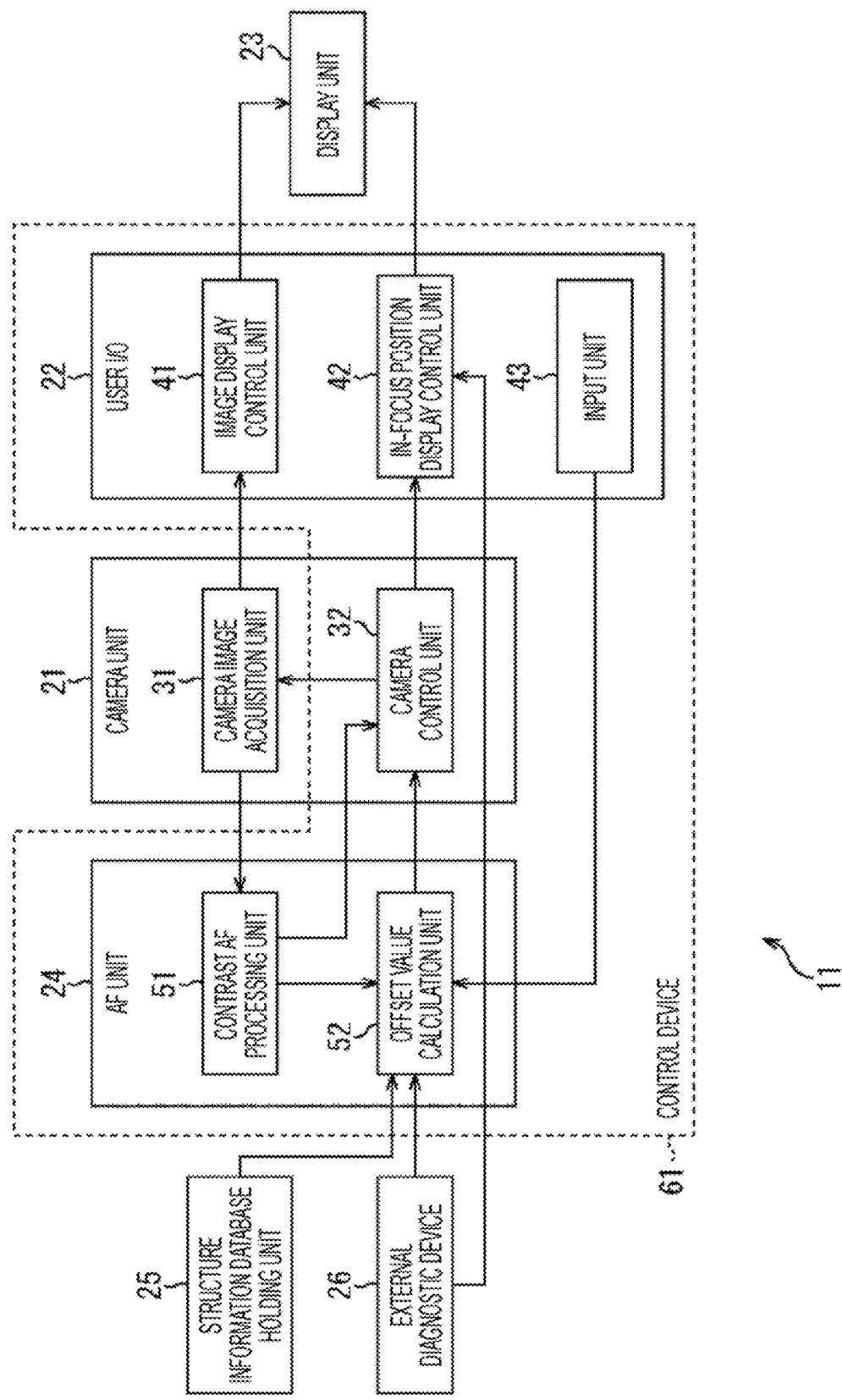
FIG. 1 is a diagram showing a configuration example of a surgical microscope system.

FIG. 1 is a diagram showing a configuration example of one embodiment of a surgical microscope system to which the present technology is applied.

The surgical microscope system 11 shown in FIG. 1 is, for example, an ophthalmic surgical microscope system including a video surgical microscope for observing an eye of a patient that is a surgical operation target before and during the surgical operation.

The surgical microscope system 11 includes a camera unit 21, a user input/output (I/O) 22, a display unit 23, an AF unit 24, a structure information database holding unit 25, and an external diagnostic device 26.

The camera unit 21 acquires an observation image obtained by observing an eye of a patient that is an observation target, that is, a surgical operation target with a microscope as a front image. Note that the following describes, as an example, a case where bright-field observation is performed as an example of microscope observation of an eye. However, microscope observation of an eye is not limited to bright-field observation and may be any other observation as long as the observation is performed by focusing on a desired region of the eye.

The camera unit 21 includes a camera image acquisition unit 31 and a camera control unit 32. For example, the camera image acquisition unit 31 constitutes at least part of the video surgical microscope.

The camera image acquisition unit 31 includes, for example, an observation optical system and an image sensor that constitute the video surgical microscope, an image processing unit that performs various types of processing on a captured image, and the like. The camera image acquisition unit 31 acquires the front image, which is a bright-field image of the patient's eye that is an observation target.

For example, during bright-field observation of the eye, illumination light output from a light source (not shown) is applied to the eye, which is an observation target, and the illumination light is reflected by each region of the eye to become observation light. The observation light is guided to an observation optical system of the video surgical microscope and enters an image sensor that constitutes the camera of the video surgical microscope.

The image sensor receives the observation light incoming from the eye via the observation optical system and photoelectrically converts the received light to capture the front image of the eye as a subject, and outputs the obtained front image, in more detail, an image signal of the front image. Then, the image processing unit of the camera image acquisition unit 31 performs various types of image processing such as white balance adjustment on the front image output from the image sensor to obtain the final front image.

On acquisition of the front image (observation image) of the eye that is an observation target in this way, the camera image acquisition unit 31 supplies the acquired front image to the user I/O 22 and the AF unit 24.

The camera control unit 32 performs focus control (AF control) by controlling the camera image acquisition unit 31 on the basis of the focus position of the camera of the video surgical microscope supplied from the AF unit 24, in more detail, information regarding the focus position of a microscope object lens that constitutes the observation optical system.

Specifically, for example, as information regarding the focus position of the camera of the video surgical microscope (video camera), focus position information indicating the focus position of the microscope object lens to be a destination in the camera image acquisition unit 31 is supplied from the AF unit 24 to the camera control unit 32.

The camera control unit 32 performs focus control (focus position adjustment) by moving the microscope object lens that functions as the focus lens of the camera in an optical axis direction such that the actual focus position of the microscope object lens is the focus position indicated by the focus position information.

Note that hereinafter, the focus position of the microscope object lens (camera) that changes in the optical axis direction by moving the microscope object lens of the camera image acquisition unit 31, that is, the in-focus position is also referred to as a camera focus position.

The user I/O 22 receives an operation input by the user and controls the display of an image and the like on the display unit 23. The user I/O 22 includes an image display control unit 41, an in-focus position display control unit 42, and an input unit 43.

The image display control unit 41 superimposes various pieces of information and images on the front image supplied from the camera image acquisition unit 31 as necessary to generate a display front image. Note that the front image obtained by the camera image acquisition unit 31 may be used as it is as the display front image.

The image display control unit 41 supplies the display front image to the display unit 23 and controls the display of the display front image on the display unit 23.

The in-focus position display control unit 42 receives the supply of the camera focus position information, which is information indicating the camera focus position, from the camera control unit 32, and receives the supply of examination information obtained from the external diagnostic device 26 by a predetermined examination for the eye and the like.

The in-focus position display control unit 42 uses the examination information and the camera focus position information as appropriate to generate an in-focus position display image, which is an image indicating the camera focus position in a cross section of the eye (tomographic plane) that is an observation target, that is, the in-focus position of the camera (observation optical system). The in-focus position display control unit 42 supplies the generated in-focus position display image to the display unit 23 and controls the display of the in-focus position display image on the display unit 23.

For example, it is assumed that, as the examination information, the in-focus position display control unit 42 is supplied with a tomographic image, which is an image of a cross section of the patient's eye. In this case, the in-focus position display control unit 42 generates an image in which information indicating the current camera focus position on the tomographic image is superimposed on the tomographic image as the in-focus position display image.

Note that the image of the tomographic plane of the eye on the in-focus position display image does not have to be a tomographic image of the actual patient's eye, but may of course be a general eye tomographic image, that is, an anatomical drawing of the eyeball and the like.

The input unit 43 includes, for example, an input device such as a touch panel, a mouse, a button, a keyboard, and a switch superimposed on the display screen of the display unit 23, which is operated by a user such as an operator performing a surgical operation, and outputs input information according to the user's operation.

For example, according to the user's operation, the input unit 43 generates, as the input information, information indicating a target focus position that is the position of the eye region that is an observation target on which the user desires to focus, that is, the position of the eye region (eye organ) corresponding to the target camera focus position. The input unit 43 supplies the generated information to the AF unit 24.

The display unit 23 includes, for example, a display such as a liquid crystal display device, and displays the display front image supplied from the image display control unit 41 and the in-focus position display image supplied from the in-focus position display control unit 42.

Note that the display front image and the in-focus position display image may be displayed in areas different from each other on one display screen of the display serving as the display unit 23, or the display front image and the in-focus position display image may be displayed on displays different from each other serving as the display unit 23. That is, the display on which the display front image is displayed and the display on which the in-focus position display image is displayed may be different from each other. Moreover, the display front image and the in-focus position display image may be displayed side by side in the display unit 23 at the same time, or may be displayed at different timing.

The AF unit 24 performs AF processing on the basis of the front image supplied from the camera image acquisition unit 31. The AF unit 24 includes a contrast AF processing unit 51 and an offset value calculation unit 52.

The contrast AF processing unit 51 performs AF processing on the basis of the front image supplied from the camera image acquisition unit 31, and supplies the resulting focus position information to the offset value calculation unit 52 or the camera control unit 32.

Here, for example, as the AF processing, on the basis of a contrast evaluation value of the front image, contrast AF processing is performed to detect the camera focus position with the highest contrast evaluation value as the camera focus position that is in focus, that is, the camera focus position that is in focus. The contrast AF processing unit 51 generates the focus position information indicating the camera focus position detected by the contrast AF processing, and supplies the focus position information to the offset value calculation unit 52 or the camera control unit 32.

Note that a case where the contrast AF processing is performed as the AF processing will be described as an example here, but the AF processing is not limited to this case. Another AF processing such as phase difference AF processing may be performed.

The offset value calculation unit 52 generates final focus position information on the basis of the input information indicating the target focus position supplied from the input unit 43, the focus position information supplied from the contrast AF processing unit 51, structure information of the eyeball supplied from the structure information database holding unit 25, and the examination information supplied from the external diagnostic device 26. The offset value calculation unit 52 supplies the final focus position information to the camera control unit 32.

For example, on the basis of at least one of the structure information and the examination information, and the target focus position, the offset value calculation unit 52 calculates, as the offset value, the distance from the camera focus position indicated by the focus position information supplied from the contrast AF processing unit 51 to the target focus position. In other words, the offset value calculation unit 52 determines the offset value.

Then, on the basis of the obtained offset value, the offset value calculation unit 52 corrects the camera focus position indicated by the focus position information supplied from the contrast AF processing unit 51, and sets the corrected camera focus position as the final camera focus position that should be a destination (target). The offset value calculation unit 52 generates the focus position information indicating the final camera focus position that should be a destination as the final focus position information, and supplies the final focus position information to the camera control unit 32.

Note that hereinafter, in particular, the focus position information output by the contrast AF processing unit 51 is also referred to as initial focus position information, and the focus position information output from the offset value calculation unit 52 is also referred to as final focus position information.

In the surgical microscope system 11, the configuration including the camera control unit 32, the AF unit 24, and the user I/O 22 described above functions as a control device 61 that controls the focus of the video surgical microscope and controls image display on the display unit 23.

The structure information database holding unit 25 holds the structure information on the eye that is a surgical operation target, that is, an observation target, and supplies the held structure information to the offset value calculation unit 52. Here, the structure information on the eye is, for example, anatomical information indicating the structure of the eyeball, such as a distance between the eye organs of the eyeball such as the cornea, the crystalline lens, or the iris, that is, the positional relationship between the eye organs.

The external diagnostic device 26 includes, for example, a device that performs examination on the patient's eye, which is used before or during the ophthalmic surgical operation on the patient's eye. The external diagnostic device 26 supplies an examination result as the examination information to the offset value calculation unit 52 and the in-focus position display control unit 42.

More specifically, for example, the external diagnostic device 26 includes an auto ref/keratometer, an eye axial length measuring device, a fundus camera, an optical coherence tomography (OCT) device, a Scheimpflug camera, and the like. Besides, the external diagnostic device 26 may be an ultrasonic tomograph that uses an ultrasonic wave to capture a tomographic image, a magnetic resonance imaging (MRI) apparatus that uses magnetism to capture a tomographic image, and the like.

For example, in a case where the external diagnostic device 26 is an auto ref/keratometer or an eye axial length measuring device, measurement results such as refractive power of the eye and the eye axial length are obtained as the examination information.

Furthermore, for example, in a case where the external diagnostic device 26 is a fundus camera, an OCT device, or a Scheimpflug camera, as the examination information, a fundus image, which is an image of the fundus of the patient, and a tomographic image, which is an image of the tomographic plane of the patient's eye, are obtained.

Note that the OCT device as the external diagnostic device 26 may be integrated with the video surgical microscope. In such a case, the external diagnostic device 26 can obtain not only the tomographic image before the surgical operation of the eye but also the tomographic image during the surgical operation of the eye.

<Operation of Each Part of the Surgical Microscope System>

Subsequently, the operation of each part of the surgical microscope system 11 shown in FIG. 1 will be described.

For example, in a case where the camera image acquisition unit 31 acquires the front image with the eye that is an observation target as a subject, if the user operates the input unit 43 to input the target focus position, processing of focusing on the target focus position is performed. This processing is performed every time the target focus position is changed.

Here, as a method of inputting the target focus position by the user, for example, a method by which the user selects one organ to be focused from a list of a plurality of eye organs and sets the position of the organ as the target focus position is considered.

In this case, for example, the image display control unit 41 generates an organ list displaying a list of organs of the eye (eye organs), such as the cornea and crystalline lens, which are candidates for the target focus position, and causes the display unit 23 to display the organ list. Note that the organ list may be displayed on the display front image in superimposition on the front image, or may be displayed as an image different from the display front image. Besides, the organ list may be displayed in superimposition on the in-focus position display image by the in-focus position display control unit 42.

When the organ list is displayed, the user operates the input unit 43 to select one organ to be focused from the organ list, that is, one organ to be the target focus position. Then, in response to the user's operation, the input unit 43 generates, as input information, information indicating the organ selected (designated) by the user, that is, information indicating the target focus position, and supplies the input information to the offset value calculation unit 52.

Furthermore, for example, as another input method of the target focus position, a method by which the user makes a selection from the tomographic image of the eyeball by graphical user interface (GUI) or touch operation is also considered.

In such a case, for example, the in-focus position display control unit 42 causes the display unit 23 to display a general eye tomographic image, that is, an image of the tomographic plane of the eye, and the in-focus position display image. Then, the user operates the input unit 43 to designate (select) the position of the eye organ to be focused on the tomographic image or the in-focus position display image displayed on the display unit 23.

The input unit 43 generates, as the input information, information indicating the organ at the position designated by the user, that is, the target focus position, in response to the user's operation, and supplies the information to the offset value calculation unit 52.

Note that, for example, in a case where the organ at the target focus position is designated on the tomographic image, the user I/O 22 may in advance hold information indicating the correspondence between areas in the tomographic image and the organs, which indicates to which organ of the eye each area of the tomographic image corresponds. Then, on the basis of the held information indicating the correspondence between areas in the tomographic image and the organs, the input unit 43 can identify to which organ area the area on the tomographic image designated by the user corresponds.

Furthermore, for example, in a case where the organ at the target focus position is designated on the in-focus position display image, the input unit 43 performs image recognition processing on the in-focus position display image to identify to which organ area of the eye each area in the in-focus position display image corresponds. Therefore, on the basis of a result of the image recognition processing, the input unit 43 can identify to which organ area the area on the in-focus position display image designated by the user corresponds.

Note that the image recognition processing and the like performed in this case on the in-focus position display image for identifying the eye organ corresponding to the target focus position may be performed by the offset value calculation unit 52.

When the target focus position is input, the camera image acquisition unit 31 subsequently starts to acquire the front image. The front image acquired by the camera image acquisition unit 31 is supplied to the contrast AF processing unit 51 and also to the image display control unit 41. The image display control unit 41 generates the display front image on the basis of the supplied front image and causes the display unit 23 to display the display front image.

When the front image is acquired in this way, the contrast AF processing is performed on the front image.

In the contrast AF processing, the camera focus position is adjusted such that a predetermined eye organ or a surgical tool area is focused in the subject area on the front image. Here, the organ to be focused, that is, the organ that is an in-focus target may be the same as the organ of the target focus position or may be a different organ.

Specifically, the contrast AF processing unit 51 extracts an initial in-focus area from the front image and performs the contrast AF processing on the initial in-focus area. That is, some area of the front image is set as the initial in-focus area, and the contrast AF processing is performed only on the initial in-focus area.

In the contrast AF processing, the camera control unit 32 controls the camera image acquisition unit 31 to sequentially move the camera focus position to the position indicated by the initial focus position information supplied from the contrast AF processing unit 51.

The camera image acquisition unit 31 acquires the front image at each camera focus position while moving the camera focus position under the control of the camera control unit 32.

The contrast AF processing unit 51 calculates the contrast evaluation values indicating the degree of contrast for the initial in-focus area of the front image for the front images obtained at a plurality of respective camera focus positions different from each other, and detects the camera focus position with the highest contrast evaluation value. In other words, the contrast AF processing unit 51 detects the camera focus position where the contrast of the initial in-focus area is the highest.

The camera focus position detected by the contrast AF processing in this way is the camera focus position in a state where an area of the eye organ or surgical tool included in the initial in-focus area is in focus, that is, a state of being focused on the eye organ or surgical tool. Hereinafter, the camera focus position detected by the contrast AF processing will be particularly referred to as initial in-focus position $d_{init}$.

The contrast AF processing unit 51 supplies the initial focus position information indicating the initial in-focus position $d_{init}$ obtained by the contrast AF processing to the offset value calculation unit 52. It can be said that such a contrast AF processing unit 51 functions as an initial in-focus position detection unit that detects the camera focus position as the initial in-focus position $d_{init}$ when focused on the predetermined subject included in the initial in-focus area by the contrast AF processing.

Note that the initial in-focus area is, for example, an area in which focus position adjustment can be performed with high precision by the contrast AF processing, that is, an area that can be focused with high precision. The initial in-focus area is also an area including a subject whose rough position can be identified in a depth direction in the eyeball, that is, in the optical axis direction of the microscope object lens.

Here, the area that can be focused with high precision is, for example, an area having a high contrast in the front image or an area including many (strong) edges having a high correlation with the contrast.

The contrast AF processing unit 51 can identify an area including many edges and an area with high contrast by performing edge detection or contrast evaluation on the front image. In such an area, it is possible to perform focus position adjustment with high precision. Note that it is known that the correlation between edge and contrast is high, and that contrast is generally high in an area including many edges.

Furthermore, in the front image, an area that includes a subject whose rough position can be identified in the depth direction can be identified by image recognition and the like. The subject mentioned here is, for example, a region such as an eye organ, a surgical tool for the ophthalmic surgical operation, and the like.

For example, by performing image recognition on the front image, the contrast AF processing unit 51 can identify to which organ of the eye or which area of the surgical tool each area in the front image corresponds.

When the organ or surgical tool included in each area as a subject is identified, it is possible to identify whether or not the rough position of the organ or surgical tool in the depth direction can be identified. Here, the organ or surgical tool whose rough position in the depth direction can be identified is, for example, an organ or surgical tool that allows identification to which area on the tomographic image as the examination information the area of the organ or surgical tool corresponds.

Furthermore, the subject in the front image is the patient's eye or surgical tool, and the composition of the front image will be determined to some extent depending on the type of surgical operation for the eye and the technique and the like used in the surgical operation. Moreover, if it is known whether or not the rough position of each organ in the depth direction can be identified and the technique of the surgical operation is identified, the rough position of each surgical tool in the depth direction is also known.

Therefore, on the basis of information regarding the surgical operation such as the type of surgical operation and the technique, the contrast AF processing unit 51 can identify the area in the front image including the eye organ or the surgical tool whose rough position in the depth direction can be identified. In this case, for example, in the front image, the area that is determined for the information regarding the surgical operation such as the type of surgical operation and the technique is the area including the eye organ or the surgical tool whose rough position in the depth direction can be identified.

Hereinafter, the condition that the focus position adjustment can be performed with high precision and that the eye organ or the surgical tool whose rough position in the depth direction can be identified is included in the area is referred to as an extraction condition.

If the initial in-focus area satisfies the extraction condition on the front image, the initial in-focus area may be a predetermined area, an area manually designated by the user by GUI, touch operation, and the like on the display front image and the like, or an area identified by the contrast AF processing unit 51 performing image processing such as image recognition or edge detection on the front image.

The area assumed as the initial in-focus area is the area of the eye organ surface or the area of the surgical tool.

As one example, for a cataract surgical operation (surgical operation of the anterior segment), the blood vessel on the sclera, the iris area, and the like may be used as the initial in-focus area, and for a retino-vitreous surgical operation (fundus surgical operation), the area of vascular structure on the retina and the like may be used as the initial in-focus area.

Furthermore, the area on the surgical tool that performs treatment such as a knife and I has a high contrast and can satisfy the extraction condition, and therefore it is considered to set the area that includes some or all of these surgical tools as the initial in-focus area.

Figure 2:
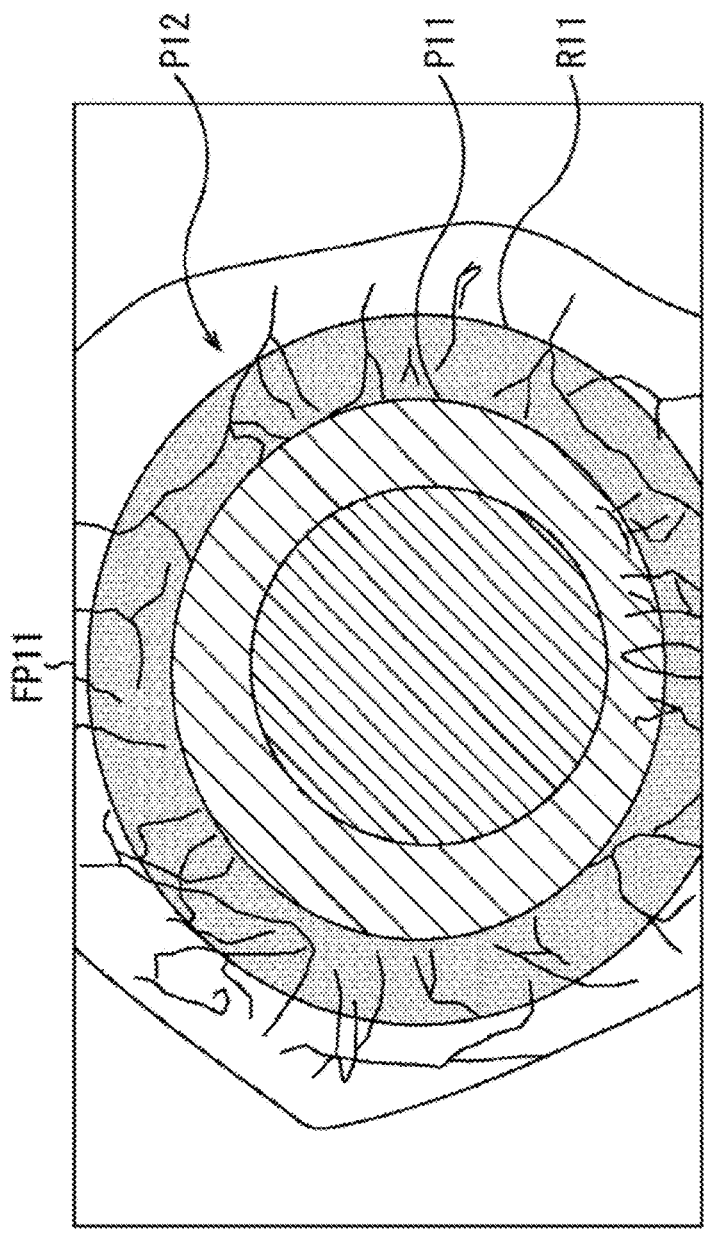
FIG. 2 is a view showing an example of an initial in-focus area.
Figure 3:
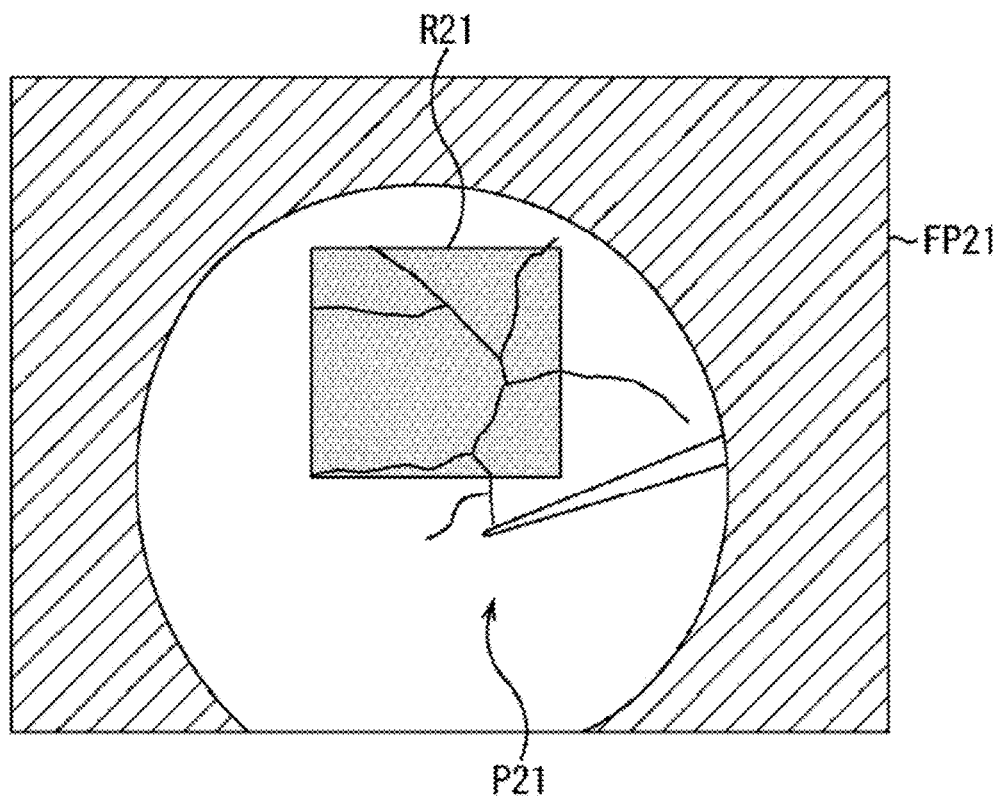
FIG. 3 is a view showing an example of the initial in-focus area.
Figure 4:
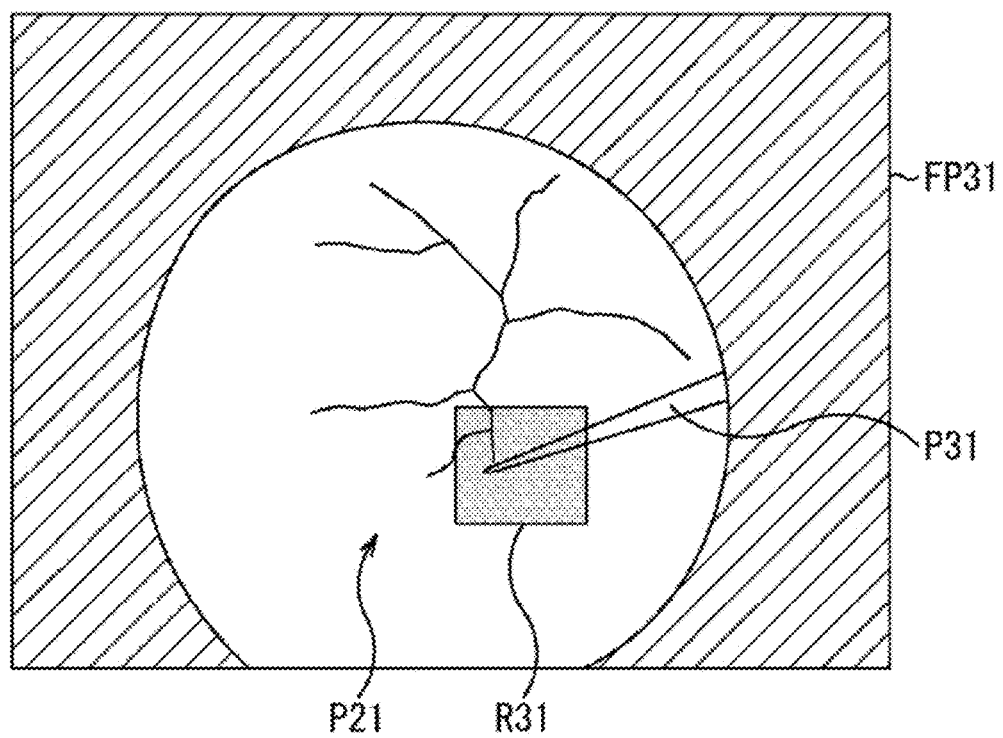
FIG. 4 is a view showing an example of the initial in-focus area.

Specifically, for example, the areas shown in FIGS. 2, 3, and 4 can be used as the initial in-focus area. Note that in FIGS. 2 to 4, parts corresponding to each other are denoted with the same reference symbol, and the description thereof will be appropriately omitted.

In the example shown in FIG. 2, the cornea P11, the iris, the retina, and the like are included as a subject in the center of the front image FP11, and the area outside the circular cornea P11 is the sclera P12. A blood vessel is included as a subject in the area of the sclera P12, the contrast of the blood vessel portion is high, and it is possible to perform focus position adjustment with high precision. Furthermore, in a portion of the sclera P12 adjacent to the cornea P11, the rough position in the depth direction can be identified on the tomographic image.

Therefore, in this example, an annular area R11 adjacent to the cornea P11 in the area of the sclera P12 is set as the initial in-focus area. Note that as described above, the initial in-focus area may be a predetermined area, an area designated by the user, or an area extracted by the contrast AF processing unit 51.

For example, in a case where the initial in-focus area is the area designated by the user, in the example of FIG. 2, the image display control unit 41 causes the display unit 23 to display the display front image including at least the front image FP11.

Then, the user operates the input unit 43 to designate the display front image, that is, the area R11 in the front image FP11 as the initial in-focus area. In this case, the input unit 43 generates information indicating the area R11 designated by the user and supplies the information to the contrast AF processing unit 51, and the contrast AF processing unit 51 extracts the area R11 from the front image FP11 as the initial in-focus area on the basis of the information supplied from the input unit 43.

Furthermore, in a case where the contrast AF processing unit 51 extracts the initial in-focus area by image processing, for example, the contrast AF processing unit 51 performs image recognition processing on the front image FP11 to detect the area of the cornea P11. Then, the contrast AF processing unit 51 extracts the area R11 surrounding the cornea P11 in the front image FP11 as the initial in-focus area. At this time, for example, the range of the area that is set as the initial in-focus area is determined such that the extraction condition is satisfied on the basis of results of contrast evaluation and edge detection for the outer area of the cornea P11.

Furthermore, in the example shown in FIG. 3, the retina P21 is included in the center of the front image FP21 as a subject, and the retina P21 part includes a blood vessel. In this example, out of the area of the retina P21 part, a rectangular area R21 including a large blood vessel is set as the initial in-focus area.

The area including the blood vessel has a high contrast, and focus position adjustment can be performed with high precision. In the retina P21 part, the rough position in the depth direction can be identified on the tomographic image.

Moreover, in the example shown in FIG. 4, the retina P21 is included as a subject in the center of the front image FP31, and a surgical tool P31 inserted into the eye chamber is included as a subject on the front side of the retina P21. In this example, part of the surgical tool P31, specifically a rectangular area R31 including the tip of the surgical tool P31 is set as the initial in-focus area.

The area including the surgical tool P31 has a high contrast and focus position adjustment can be performed with high precision. At the tip of the surgical tool P31, the rough position in the depth direction can be identified on the tomographic image.

As described above, when the initial in-focus area is extracted from the front image and the contrast AF processing is performed and the initial focus position information indicating the initial in-focus position $d_{init}$ is obtained, thereafter, the offset value calculation unit 52 calculates an offset value $d_{offset}$.

The offset value $d_{offset}$ calculated by the offset value calculation unit 52 is information indicating the distance from the initial in-focus position $d_{init}$ to the target focus position in the optical axis direction of the microscope object lens (observation optical system).

When calculating the offset value $d_{offset}$, the initial focus position information indicating the initial in-focus position $d_{init}$, the input information indicating the target focus position, and at least one of the structure information and the examination information of the eyeball are used.

When the offset value calculation unit 52 calculates the offset value $d_{offset}$, the offset value calculation unit 52 corrects the initial in-focus position $d_{init}$ with the obtained offset value $d_{offset}$, and calculates the in-focus position $d_{focuss}$ that is the camera focus position that should finally be the target destination. The offset value calculation unit 52 supplies the final focus position information indicating the in-focus position $d_{focuss}$ to the camera control unit 32.

Here, the in-focus position $d_{focuss}$ is a camera focus position when focusing on the eye organ at the target focus position in the front image, and can be obtained by calculating Equation (1) below.

[Equation 1]

$$d_{focuss} = d_{init} + d_{offset} \qquad (1)$$

The camera control unit 32 controls the camera image acquisition unit 31 to move the microscope object lens such that the camera focus position becomes the in-focus position $d_{focuss}$ indicated by the final focus position information, thereby making it possible to focus on the eye organ designated by the user as the target focus position in the front image.

In this way, in the surgical microscope system 11, after once focusing on a subject that can be easily focused, the offset value $d_{offset}$ between the subject and the target focus position is determined, and the final in-focus position $d_{focuss}$ is calculated from the offset value $d_{offset}$.

With this operation, even in a case where a region (organ) of the eye that is a subject to be focused is a transparent body, with an arbitrary region of the eye as the desired target focus position, the target focus position can be focused at high speed and with high precision. The method according to the present technology is particularly useful when the target focus position is an eye organ (organ) located inside the eye, that is, inside the corneal endothelium. The eye organ inside the corneal endothelium mentioned here is an organ on the retina side of the corneal endothelium in the eyeball.

Note that in the surgical microscope system 11, after the contrast AF processing is performed, the resultant initial in-focus position $d_{init}$ is used to calculate the in-focus position $d_{focuss}$ and the camera focus position is moved to the in-focus position $d_{focuss}$. In more detail, a series of focus adjustment processes to move the camera focus position to the in-focus position $d_{focuss}$, including the contrast AF processing, will be the AF processing performed in the surgical microscope system 11.

Here, a specific example of calculating the offset value $d_{offset}$ will be described.

First, the relationship between the initial in-focus position $d_{init}$, the offset value $d_{offset}$, and the in-focus position $d_{focuss}$ will be described with reference to FIG. 5.

Figure 5:
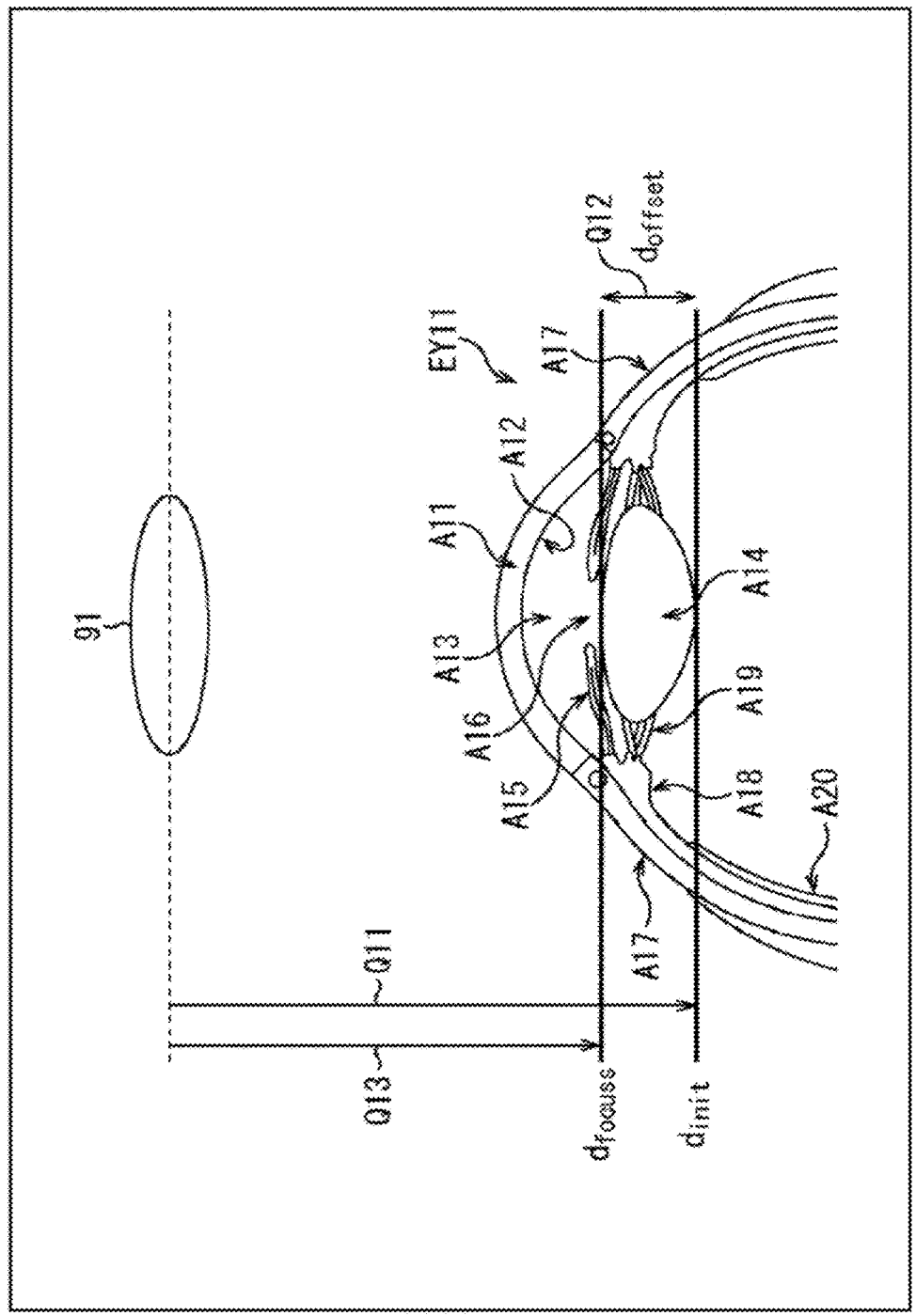
FIG. 5 is a view showing a relationship between an initial in-focus position, an offset value, and an in-focus position.

The example shown in FIG. 5 shows a cross section of the eye EY11 of the patient, which is a subject of an observation target, and a microscope object lens 91 that constitutes the camera image acquisition unit 31. Note that in the figure, the longitudinal direction is the optical axis direction of the microscope object lens 91, that is, the depth direction.

For example, in FIG. 5, a portion indicated by an arrow A11 is the cornea of the eye EY11, and in particular, an inner portion of the cornea indicated by an arrow A12 is the corneal endothelium.

Furthermore, the inner portion of the cornea of the eye EY11, that is, the portion indicated by an arrow A13 is the eye chamber, and a portion indicated by an arrow A14 immediately below is the crystalline lens. Moreover, a portion indicated by an arrow A15 and provided so as to cover a portion of a front membrane of the crystalline lens is the iris, and a hole portion indicated by an arrow A16 in the center of the iris is the pupil.

Furthermore, a portion around the outside of the cornea of the eye EY11, indicated by an arrow A17, is the sclera. A portion indicated by an arrow A18 near the crystalline lens inside the eyeball is the ciliary muscle. A portion indicated by an arrow A19 connecting the ciliary muscle to the crystalline lens is the ciliary zonule. Moreover, an inner portion of the eyeball indicated by an arrow A20 is the retina.

Now, it is assumed that a front membrane portion of the crystalline lens, which is a transparent body in the eye EY11, that is, in the diagram of the crystalline lens indicated by the arrow A14, the upper surface portion called the anterior capsule is designated as the target focus position.

Furthermore, it is assumed that, for example, an area near the cornea in the sclera portion of the eye EY11 that is not a transparent body is the initial in-focus area, and that the position of a blood vessel on the sclera, that is, the position indicated by an arrow Q11 is detected as the initial in-focus position $d_{init}$.

Here, the initial in-focus position $d_{init}$ is, for example, the position of the detected blood vessel on the sclera with reference to a predetermined position. In other words, the initial in-focus position $d_{init}$ is the distance from the predetermined reference position in the optical axis direction (hereinafter also referred to as Z direction) of the microscope object lens 91 to the detected blood vessel position on the sclera. Note that in FIG. 5, the predetermined reference position is the position where the dotted line is drawn.

In this case, the value indicating the distance from the initial in-focus position $d_{init}$ to the membrane (anterior capsule) on the front surface of the crystalline lens, which is a target focus position, that is, the value indicated by an arrow Q12 is set as the offset value $d_{offset}$. In the example of FIG. 5, the offset value $d_{offset}$ is a negative value.

Then, the position obtained by Equation (1) from the initial in-focus position $d_{init}$ and the offset value $d_{offset}$ thus obtained is set as the final in-focus position $d_{focuss}$. Here, the in-focus position $d_{focuss}$ should be the position indicated by an arrow Q13, and the in-focus position $d_{focuss}$ should be the target focus position designated by the user.

In this way, the offset value $d_{offset}$ is the distance in the Z direction between the target focus position and the initial in-focus position $d_{init}$, and the offset value $d_{offset}$ is obtained from the anatomical information of the human eyeball, that is, information regarding the structure of the eyeball.

The information regarding the structure of the eyeball to be used to calculate the offset value $d_{offset}$ is, for example, structure information held in the structure information database holding unit 25, and the examination information obtained by the external diagnostic device 26.

For example, the tomographic image as the examination information includes each eye organ as a subject. Therefore, by performing image recognition processing and the like on the tomographic image as appropriate, the positional relationship of eye organs in the tomographic image can be identified. Therefore, it can be said that not only the structure information on the eyeball but also the tomographic image is information regarding the structure of the eyeball. Similarly, information indicating measurement results such as the eye axial length as the examination information is also information indicating the structure of the eye. Since the positional relationship of eye organs can be identified from such measurement results and the like, it can be said that the examination information such as the measurement results and the like is also information regarding the structure of the eyeball.

As a specific example, for example, a case where statistical anatomical information on a human eyeball, that is, statistical structure information indicating the eyeball structure, which is held in the structure information database holding unit 25, is used will be described.

For example, it is assumed that the information indicating the distance from the predetermined reference position of the eyeball to each organ of the eye is held in the structure information database holding unit 25 as the structure information indicating the structure of the eyeball.

Note that here, the predetermined reference position of the eyeball is the apex position of the corneal surface, that is, the position of the corneal apex. Therefore, information indicating the distance from the corneal apex to each organ, for example, the physical distance X mm from the corneal apex to the position of the blood vessel on the sclera, the physical distance Y mm from the corneal apex to the anterior capsule (membrane in front of the crystalline lens), and the like, that is, the depth position information of each organ is the structure information.

The offset value $d_{offset}$ can be calculated by referring to such eyeball structure information. Here, it is assumed that the correspondence between the position of each organ indicated by the structure information in the depth direction (Z direction) and the camera focus position is known from the optical magnification and the like of the microscope object lens 91.

For example, in the example shown in FIG. 5, the offset value calculation unit 52 identifies the distance X mm from the corneal apex to the position indicated by the initial in-focus position $d_{init}$, that is, the position of the blood vessel on the sclera on the basis of the initial in-focus position $d_{init}$ and the structure information.

Note that in a case where the eye organ (region) in the initial in-focus area, that is, the eye organ at the initial in-focus position $d_{init}$ is identified, even without using the initial in-focus position $d_{init}$, the distance from the corneal apex to the organ in the initial in-focus area can be obtained on the basis of only the structure information.

Furthermore, by referring to the structure information, the offset value calculation unit 52 identifies the distance Y mm from the corneal apex to the anterior capsule (membrane in front of the crystalline lens) that is a target focus position indicated by the input information. Then, the offset value calculation unit 52 calculates the difference (Y-X) between the distance X mm and the distance Y mm, and sets the calculated difference (Y-X) as the offset value $d_{offset}$.

Moreover, here, an example of obtaining the offset value $d_{offset}$ by using the structure information held in the structure information database holding unit 25 has been described. However, the offset value $d_{offset}$ can be similarly obtained by using the tomographic image as the examination information.

In such a case, for example, the offset value calculation unit 52 performs image recognition processing on the tomographic image as the examination information, and detects the area of the eye organ designated as the target focus position on the tomographic image. Furthermore, the offset value calculation unit 52 identifies the position corresponding to the initial in-focus position $d_{init}$ on the tomographic image by using known information including the optical magnification and the like of the microscope object lens 91 as necessary.

Even in this case, in a case where the eye organ (region) within the initial in-focus area is identified, without using the initial in-focus position $d_{init}$, from the result of image recognition processing, it is possible to estimate the position corresponding to the initial in-focus position $d_{init}$ on the tomographic image, that is, the position of the organ included in the initial in-focus area on the tomographic image.

The offset value calculation unit 52 calculates the distance from the position corresponding to the initial in-focus position $d_{init}$ on the tomographic image to the position of the eye organ designated as the target focus position, and calculates the offset value $d_{offset}$ from the calculated distance.

In particular, in a case where the tomographic image obtained during the surgical operation is used to calculate the offset value $d_{offset}$, it is possible to deal with structural changes of the patient's eye such as insertion of an intraocular lens caused by the surgical operation.

Moreover, even in a case where the initial in-focus position $d_{init}$ is the position of the surgical tool, the offset value $d_{offset}$ can be obtained in a similar manner to the case where the region corresponding to the initial in-focus position $d_{init}$ is an eye organ. In particular, in a case where the initial in-focus position $d_{init}$ is the position of the surgical tool, the offset value $d_{offset}$ can be obtained using the type of surgical tool and context information indicating what kind of treatment (technique) is being performed.

For example, the type of surgical tool and the context information may be obtained by the user operating the input unit 43 and inputting the information, and the offset value calculation unit 52 acquiring the input information according to the input operation. Furthermore, the offset value calculation unit 52 may perform image recognition processing on the tomographic image or front image supplied as the examination information to obtain the type of surgical tool or the context information.

Specifically, it is assumed that, for example, a crystalline lens suction device is used as the surgical tool, and a needle tip portion of the crystalline lens suction device is included in the initial in-focus area. In this case, the offset value calculation unit 52 identifies the needle tip of the crystalline lens suction device as a surgical tool by performing image recognition processing on the tomographic image obtained during the surgical operation. The offset value calculation unit 52 sets the position of the needle of the crystalline lens suction device on the tomographic image obtained as a result of the identification as the position corresponding to the initial in-focus position $d_{init}$. Note that the initial in-focus position $d_{init}$ may also be used in identifying the position corresponding to the initial in-focus position $d_{init}$.

Besides, the contrast AF processing unit 51 may also extract the initial in-focus area by using the type of surgical tool or the position of the surgical tool obtained as a result of image recognition processing on the front image or tomographic image, the context information obtained from the input information, and the like.

In that connection, for example, in a case where the offset value $d_{offset}$ is obtained by using the structure information and the like held in the structure information database holding unit 25, since the anatomy (structure) of the eyeball varies from person to person, it may not always be possible to obtain the accurate offset value $d_{offset}$ for all patients.

Therefore, for example, a more accurate offset value may be obtained by correcting the offset value $d_{offset}$ by using patient-specific information obtained by the external diagnostic device 26.

As a specific example, for example, as patient-specific information used as the examination information, patient's personal information showing the characteristics of the patient, patient's eyeball shape information showing the shape of the patient's eyeball, tomographic image of the patient's eye, and the like are considered.

Here, the patient personal information includes, for example, information including age, sex, physique, race, and the like of the patient, and the patient's eyeball shape information is numerical information and the like indicating the eyeball shape such as the eye axial length and anterior chamber depth of the patient's eye obtained in the examination before the surgical operation. Note that the eye axial length is the distance from the corneal apex to the retina in the Z direction, and the anterior chamber depth is the distance from the corneal endothelium to the anterior capsule.

Furthermore, the tomographic image as patient-specific information may be, for example, a tomographic image and the like acquired (measured) by an OCT device or the Scheimpflug camera as the external diagnostic device 26 before or during the surgical operation of the patient's eye.

In this case, for example, if predetermined variables a and b are values that depend on patient-specific information, the corrected offset value d'offset can be expressed by Equation (2) below.

[Equation 2]

$$d'_{offset} = a d_{offset} + b \quad (2)$$

For example, the offset value calculation unit 52 calculates the variables a and b for each patient on the basis of the examination information supplied from the external diagnostic device 26 as patient-specific information, that is, the patient individual information, the patient eyeball shape information, and the tomographic image described above.

Then, the offset value calculation unit 52 calculates the corrected offset value d'offset by calculating Equation (2) described above on the basis of the calculated variables a and b and the offset value $d_{offset}$. Furthermore, the offset value calculation unit 52 calculates the final in-focus position $d_{focuss}$ by performing calculation similar to Equation (1) on the basis of the obtained offset value d'$_{offset}$ and the initial in-focus position $d_{init}$.

Note that since the eyeball structure of the patient changes depending on the result of treatment during the surgical operation, in order to respond to the change, the variables a and b to be used for correcting the offset value $d_{offset}$ may be recalculated or updated at appropriate timing.

Moreover, in the surgical microscope system 11, when the camera focus position is moved to the in-focus position $d_{focuss}$ and the focus is adjusted to the target focus position, the display unit 23 displays the in-focus position display image.

For example, in a state where a transparent body such as the anterior capsule is in focus in the front image, it is difficult for the user who is an operator to determine the in-focus position from the front image even when looking at the display front image. Therefore, the surgical microscope system 11 allows the user to intuitively determine the in-focus position by displaying the in-focus position display image showing the current in-focus position.

As described above, the in-focus position display image may be an image in which the information indicating the camera focus position is superimposed on the actual tomographic image of the patient obtained by the external diagnostic device 26, or may be an image in which the information indicating the camera focus position is superimposed on the general eyeball tomographic image (anatomical drawing).

Note that the tomographic image to be used to generate the in-focus position display image may be obtained by the external diagnostic device 26 before the surgical operation of the patient's eye, that is, before the surgical operation, or by the external diagnostic device 26 during the surgical operation.

Figure 6:
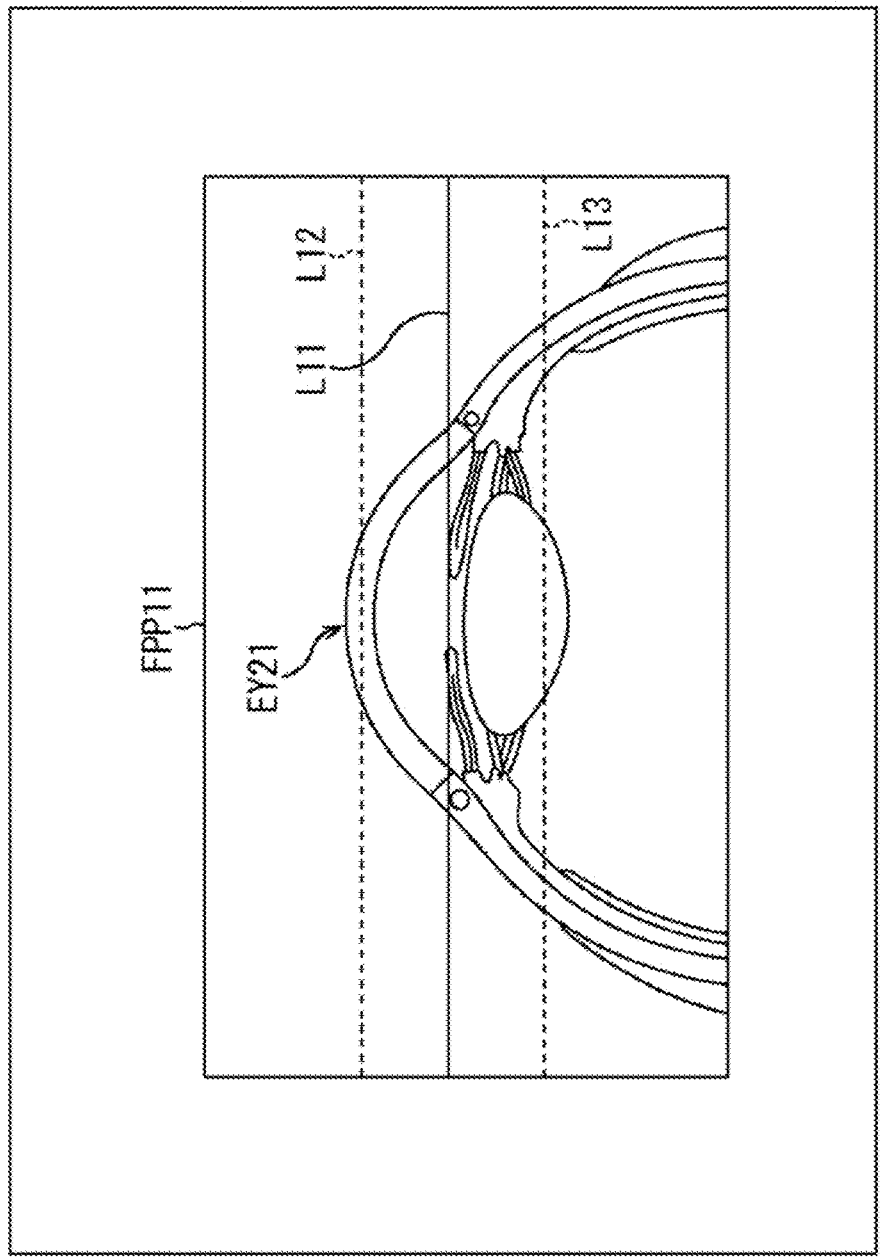
FIG. 6 is a view showing an example of an in-focus position display image.
Figure 7:
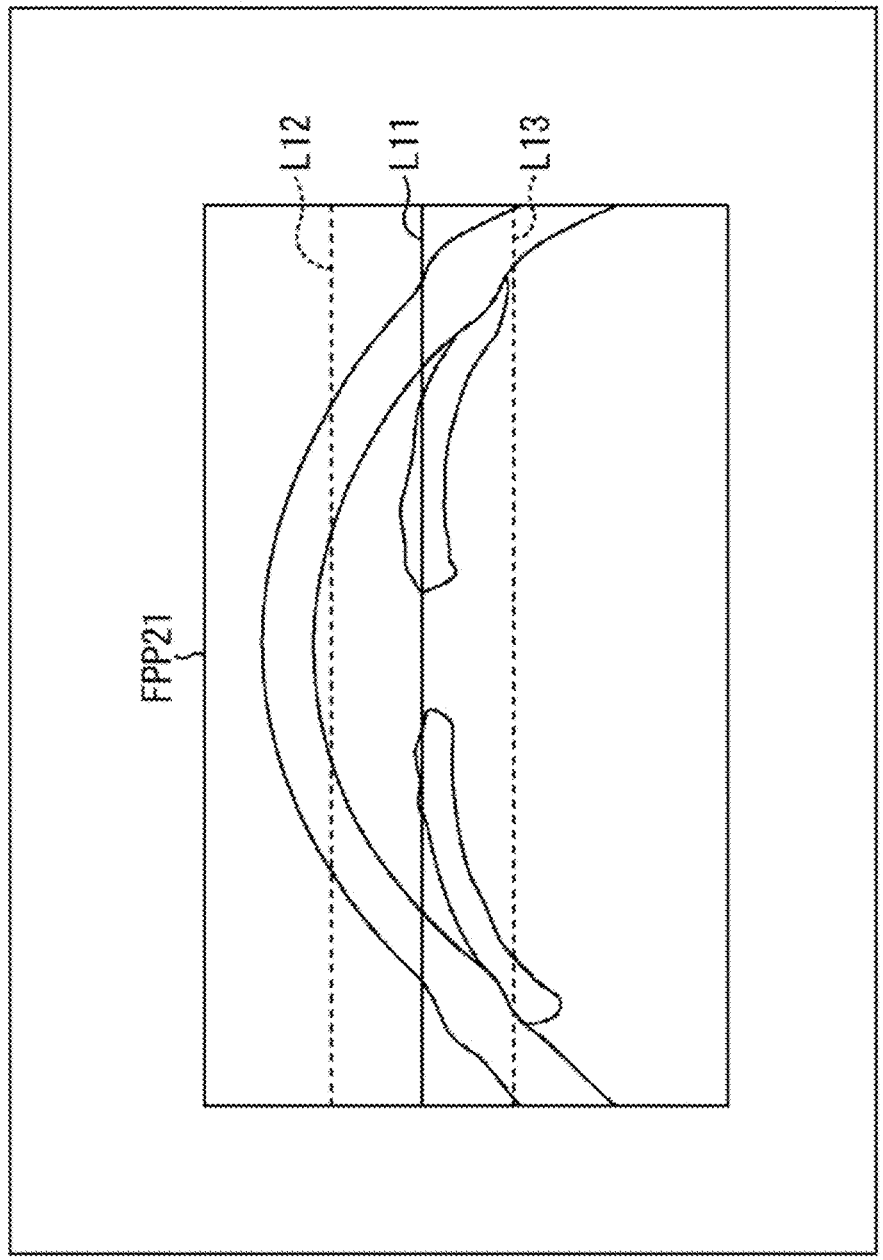
FIG. 7 is a view showing an example of the in-focus position display image.
Figure 8:
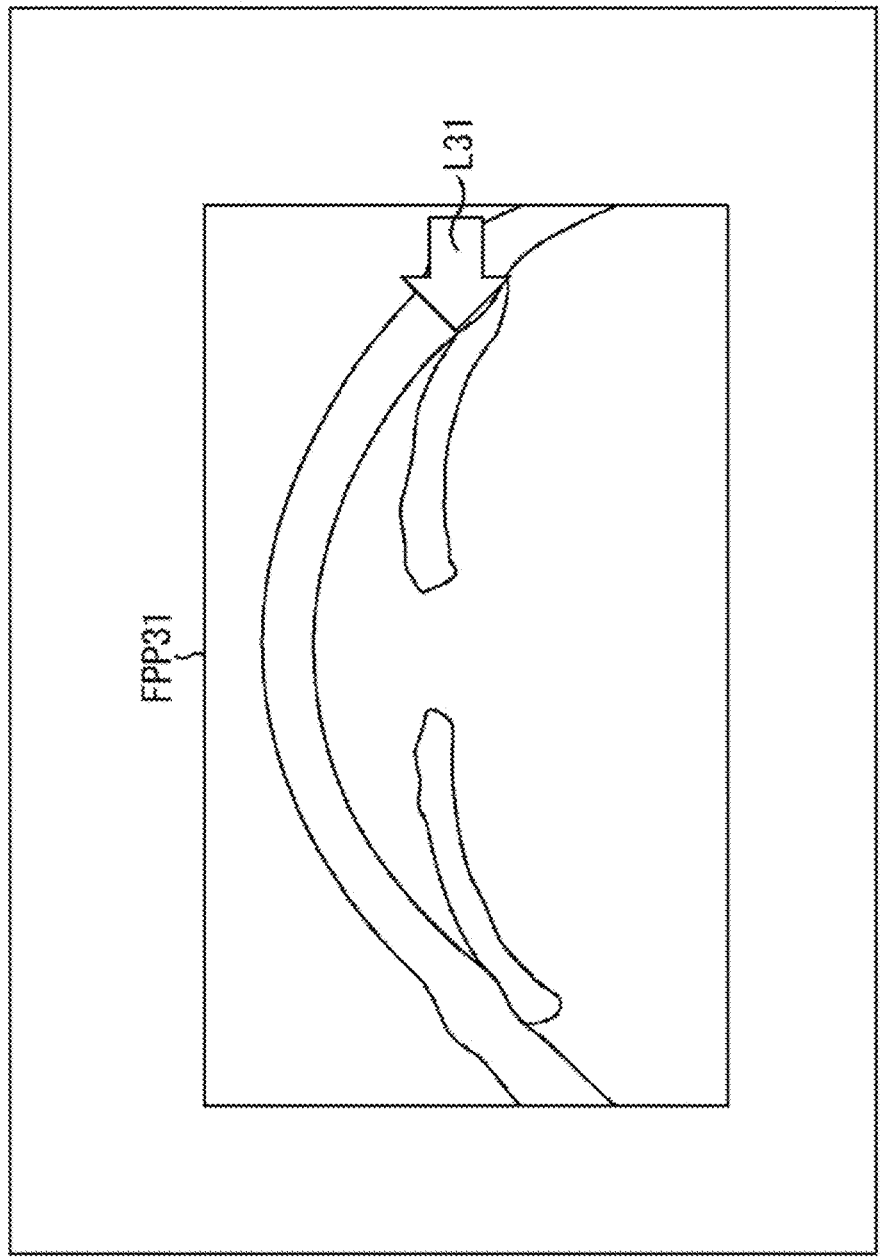
FIG. 8 is a view showing an example of the in-focus position display image.

Furthermore, specific examples of the in-focus position display image, for example, shown in FIGS. 6, 7, and 8, and the like can be considered. Note that in FIGS. 6 to 8, parts corresponding to each other are denoted with the same reference symbol, and the description thereof will be appropriately omitted.

In the example shown in FIG. 6, the in-focus position display image FPP11 is an image in which straight lines L11 to L13 indicating the current camera focus position, that is, the in-focus position $d_{focuss}$ is displayed on the general tomographic image of an eyeball. In particular, in the in-focus position display image FPP11, the longitudinal direction is the Z direction in the figure.

FIG. 6, which is a cross-sectional view of the eyeball, shows an eye EY21 as a tomographic image of the eyeball, and the straight line L11 is drawn at a position corresponding to the in-focus position $d_{focuss}$ in the eye EY21. Furthermore, the dotted straight lines L12 and L13 are drawn at the positions of end portions of the area having a predetermined width centered on the straight line L11. That is, the straight line L11 is located halfway between the straight lines L12 and L13.

In particular, here, the position of the straight line L11 is the position corresponding to the in-focus position $d_{focuss}$. By looking at the straight line L11, the user can intuitively determine that the position of the region where the straight line L11 is present is in focus in the front image.

Furthermore, the area between the straight line L11 and the straight line L12, and the area between the straight line L11 and the straight line L13 are roughly in focus. Therefore, the user can intuitively determine how deep focus is achieved in the front image by looking at the straight line L12 or the straight line L13.

In the in-focus position display image In FPP11, when the in-focus position $d_{focuss}$ changes, the straight lines L11 to L13 also move in the longitudinal direction in the figure in response to the change. By displaying such an in-focus position display image FPP11 side by side with the display front image at the same time, the in-focus position $d_{focuss}$ can be easily determined and the usability of the surgical microscope system 11 can be improved.

Note that a band-shaped semi-transparent color image of a predetermined color may be superimposed and displayed on the area between the straight line L12 and the straight line L13, and the display density of the color of each area of the color image may be set at the density according to the degree of focus.

For example, if an area is displayed darker as the degree of focus in the area increases, the area near the straight line L11 is displayed with higher density in the color image, and an area closer to the straight line L12 or the straight line L13, that is, an area farther from the straight line L11 is displayed with lower density.

Furthermore, in the example shown in FIG. 7, the in-focus position display image FPP21 displays the current camera focus position on the tomographic image of the actual patient's eye, that is, the straight lines L11 to L13 indicating the in-focus position $d_{focuss}$. In particular, in the in-focus position display image FPP21, the longitudinal direction is the Z direction in the figure.

Moreover, in the example shown in FIG. 8, the in-focus position display image FPP31 displays the current camera focus position, that is, an arrow L31 indicating the in-focus position $d_{focuss}$ on the tomographic image of the actual patient's eye.

In particular, in the in-focus position display image FPP31, the longitudinal direction is the Z direction in the figure, and the position of the arrow L31 corresponds to the in-focus position $d_{focuss}$. Furthermore, in the in-focus position display image FPP31, when the in-focus position $d_{focuss}$ changes, the arrow L31 also moves in the longitudinal direction in the figure according to the change. Therefore, by looking at the arrow L31, the user can intuitively determine in the front image that the position of the region where the arrow L31 is present is in focus.

Note that for example, in a case where the target focus position is input by a touch operation and the like on the in-focus position display image shown in FIG. 6, 7, or 8, the user makes input by designating the desired position of the in-focus position display image displayed on the display unit 23 by a touch operation and the like.

For example, in the example of FIG. 6, when the user designates the anterior capsule portion on the in-focus position display image FPP11 by a touch operation on the input unit 43, the designated anterior capsule portion is input as the target focus position.

<Description of Observation Processing>

Next, the overall operation of the surgical microscope system 11 will be described. That is, the observation processing by the surgical microscope system 11 will be described below with reference to the flowchart of FIG. 9. This observation processing is started when the input unit 43 is operated by the user who is an operator and the like to input the target focus position.

In step S11, the input unit 43 acquires the information indicating the target focus position input by the user in response to the operation on the input unit 43 by the user. The input unit 43 generates input information indicating the target focus position and supplies the input information to the offset value calculation unit 52.

For example, the target focus position may be input by performing a selection operation on the organ list displayed on the display unit 23, or by designating the position of a desired organ (region) on the in-focus position display image.

In step S12, the camera image acquisition unit 31 acquires the front image of the eye of an observation target, and supplies the obtained front image to the contrast AF processing unit 51 and the image display control unit 41.

Specifically, the image sensor of the camera image acquisition unit 31 captures the front image by receiving and photoelectrically converting the observation light incoming from the eye via the observation optical system. Furthermore, the image processing unit of the camera image acquisition unit 31 performs various types of image processing such as white balance adjustment on the front image obtained from the image sensor to obtain the final front image.

The image display control unit 41 generates the display front image on the basis of the front image supplied from the camera image acquisition unit 31 and supplies the display front image to the display unit 23 for display.

In step S13, the contrast AF processing unit 51 extracts the initial in-focus area from the front image supplied from the camera image acquisition unit 31.

For example, the contrast AF processing unit 51 may extract a predetermined area in the front image as the initial in-focus area, or may extract an area designated by the user in the front image as the initial in-focus area. Moreover, the contrast AF processing unit 51 may extract an area that satisfies the extraction condition in the front image as the initial in-focus area by performing image processing such as image recognition on the front image.

Note that once the initial in-focus area is determined, thereafter, while contrast AF processing is being performed, that is, while the processing of steps S12 to S16 is being repeatedly performed, areas having the same positional relationship in each front image to be processed are continuously set as the initial in-focus area.

In step S14, the contrast AF processing unit 51 calculates the contrast evaluation value for the initial in-focus area extracted from the front image in the process of step S13.

Furthermore, the contrast AF processing unit 51 detects a peak value of the contrast evaluation value on the basis of the contrast evaluation value at each camera focus position obtained by the processing in step S14 performed so far.

Since the contrast evaluation value increases as the contrast of the initial in-focus area increases, the camera focus position when the contrast evaluation value that is a peak value is obtained is the initial in-focus position $d_{init}$.

In step S15, the contrast AF processing unit 51 determines whether or not the peak value of the contrast evaluation value is detected.

In a case where the peak value of the contrast evaluation value is not detected in step S15, that is, in a case where it is determined that the initial in-focus position $d_{init}$ is not detected, thereafter, the process proceeds to step S16. In this case, the contrast AF processing unit 51 generates focus position information indicating the camera focus position, which is an appropriate destination, on the basis of the contrast evaluation value obtained so far, and supplies the focus position information to the camera control unit 32.

In step S16, the camera control unit 32 controls the camera image acquisition unit 31 on the basis of the focus position information supplied from the contrast AF processing unit 51, and adjusts the camera focus position. That is, the camera control unit 32 controls the camera image acquisition unit 31 to move the microscope object lens 91 in the optical axis direction such that the camera focus position of the microscope object lens 91 becomes the camera focus position indicated by the focus position information from the contrast AF processing unit 51.

When the camera focus position is adjusted, thereafter, the process returns to step S12, and the above process is repeated until the peak value is detected.

On the other hand, in a case where it is determined in step S15 that the peak value of the contrast evaluation value is detected, thereafter, the process proceeds to step S17.

In this case, the contrast AF processing unit 51 sets the camera focus position when the contrast evaluation value that is the detected peak value is obtained as the initial in-focus position $d_{init}$, and supplies the initial focus position information indicating the initial in-focus position $d_{init}$ to the offset value calculation unit 52.

In step S17, the offset value calculation unit 52 acquires the structure information and the examination information. That is, the offset value calculation unit 52 acquires the structure information on the eyeball from the structure information database holding unit 25, and acquires the examination information from the external diagnostic device 26.

In step S18, the offset value calculation unit 52 calculates the offset value $d_{offset}$ on the basis of the input information indicating the target focus position supplied from the input unit 43 in step S11 and the initial focus position information supplied from the contrast AF processing unit 51. At this time, the offset value calculation unit 52 calculates the offset value $d_{offset}$ by also using at least one of the structure information and the examination information acquired in step S17. Furthermore, the initial focus position information does not necessarily have to be used for calculating the offset value $d_{offset}$.

For example, the offset value calculation unit 52 performs image processing such as image recognition as necessary by using the structure information indicating the structure of the eyeball or the tomographic image as the examination information as described above, and calculates the offset value $d_{offset}$. Note that the offset value calculation unit 52 may correct the offset value $d_{offset}$ by performing the calculation of Equation (2) described above.

In step S19, the offset value calculation unit 52 calculates the in-focus position $d_{focuss}$ by calculating Equation (1) above on the basis of the offset value $d_{offset}$ obtained in step S18 and the initial in-focus position $d_{init}$ indicated by the initial focus position information.

The offset value calculation unit 52 generates the final focus position information indicating the in-focus position $d_{focuss}$ obtained in this way, and supplies the final focus position information to the camera control unit 32.

In step S20, the camera control unit 32 controls the camera image acquisition unit 31 on the basis of the final focus position information supplied from the offset value calculation unit 52, and adjusts the camera focus position. That is, the camera control unit 32 controls the camera image acquisition unit 31 to move the microscope object lens 91 in the optical axis direction such that the camera focus position of the microscope object lens 91 becomes the in-focus position $d_{focuss}$ indicated by the final focus position information.

This leads to a state where the camera focus position of the microscope object lens 91 is at the target focus position input in step S11, that is, a state where the position of the eye organ designated as the target focus position is in focus.

Furthermore, the camera control unit 32 supplies the camera focus position information indicating the in-focus position $d_{focuss}$ to the in-focus position display control unit 42. Then, the in-focus position display control unit 42 generates the in-focus position display image on the basis of the camera focus position information supplied from the camera control unit 32 and the tomographic image as the examination information from the external diagnostic device 26 or the tomographic image of the eyeball held in advance.

In step S21, the in-focus position display control unit 42 supplies the generated in-focus position display image to the display unit 23 and causes the display unit 23 to display the in-focus position display image. With this operation, for example, the in-focus position display image shown in FIG. 6, 7, or 8 is displayed. Note that the in-focus position display image may be displayed not only at timing of focusing on the target focus position, but may be continuously displayed after the acquisition of the front image is started, and may be updated every time the camera focus position changes.

After the in-focus position display image is displayed, the observation processing ends.

As described above, the surgical microscope system 11 causes the position of the predetermined organ and the like of the eye to be focused by contrast AF processing, and thereafter, the surgical microscope system 11 calculates the final in-focus position $d_{focuss}$ by obtaining the offset value $d_{offset}$ from the target focus position. With this operation, even in a case where the target focus position is a transparent body, the target focus position can be focused at high speed. That is, it is possible to focus on the desired position of the subject.

Second Embodiment

<Configuration Example of Surgical Microscope System>

Meanwhile, in a surgical microscope system 11, it is necessary to focus on an area with a high contrast in an initial in-focus area every time AF processing, that is, adjustment of a camera focus position is performed. Therefore, it is not possible to continuously maintain an in-focus state on a transparent body at a target focus position during AF processing. That is, the provision of an in-focus operative field image is temporarily suspended.

Therefore, for example, in the surgical microscope system 11, in a case where AF processing is performed frequently, such as continuous AF processing to sequentially perform AF processing to focus on the target focus position continuously, after focusing on an area with a high contrast in the initial in-focus area, an operation of focusing on the target focus position is repeated. That is, since a state where a region within the initial in-focus area is in focus and a state where the target focus position is in focus are alternately repeated, it is difficult to continuously provide an operative field that is in focus on the target focus position.

Therefore, the surgical microscope system may be provided with a camera unit for adjusting the camera focus position, that is, for AF processing, apart from a camera unit for acquiring a front image, to make it possible to follow the focus position continuously while presenting an image focused on the target focus position (front image). That is, by separating the camera unit for eye observation and the camera unit for AF processing, the front image focused on the target focus position may be continuously provided even in a case where AF processing is frequently performed.

Figure 10:
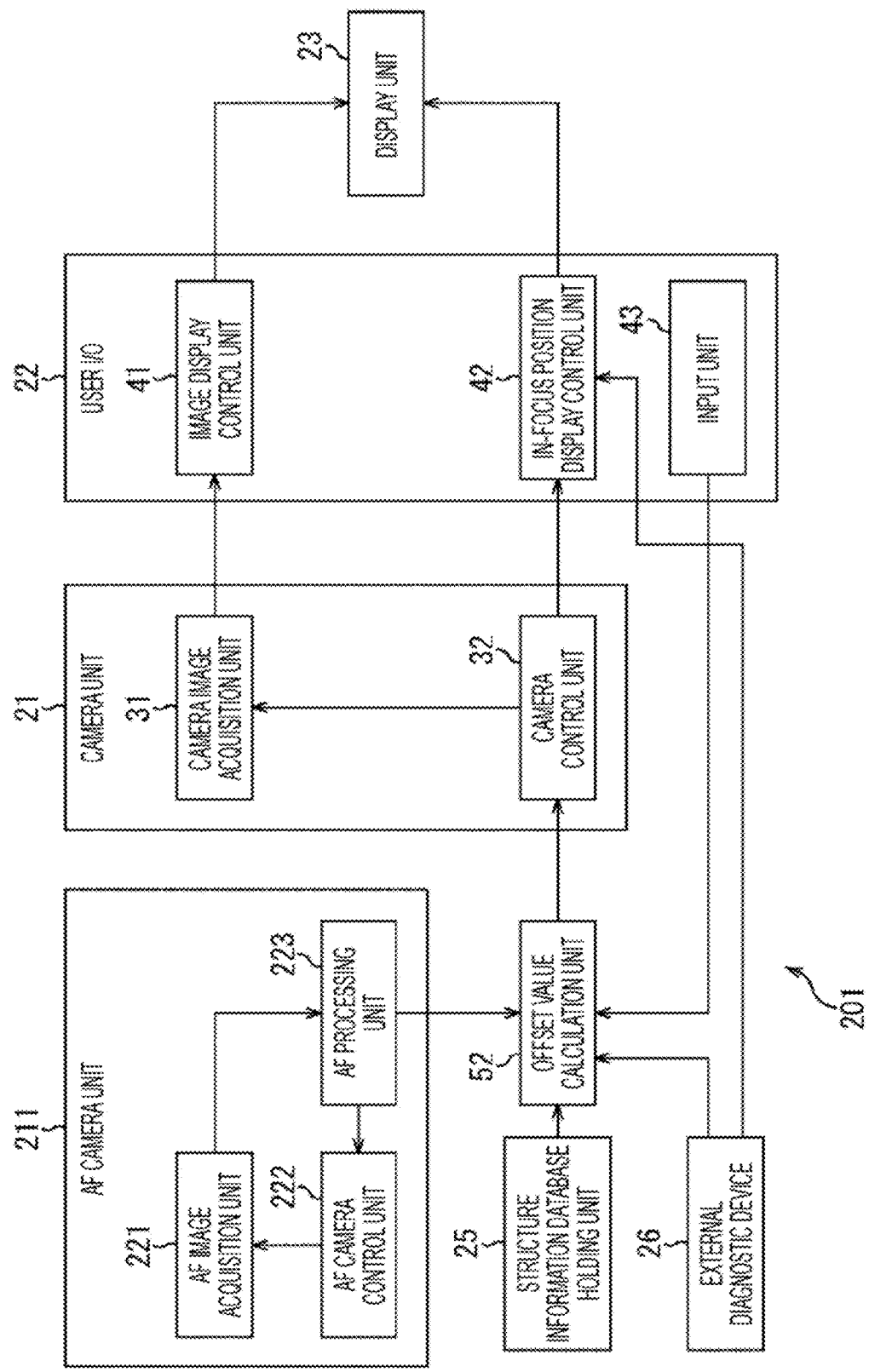
FIG. 10 is a diagram showing a configuration example of a surgical microscope system.

In such a case, the surgical microscope system to which the present technology is applied has, for example, a configuration shown in FIG. 10. Note that in FIG. 10, parts corresponding to the case in FIG. 1 are denoted with the same reference symbol, and descriptions thereof will be appropriately omitted.

The surgical microscope system 201 shown in FIG. 10 includes a camera unit 21, a user I/O 22, a display unit 23, an AF camera unit 211, a structure information database holding unit 25, an external diagnostic device 26, and an offset value calculation unit 52.

Furthermore, the camera unit 21 includes a camera image acquisition unit 31 and a camera control unit 32, and the camera image acquisition unit 31 and the camera control unit 32 perform operations similar to the case of FIG. 1.

Moreover, the user I/O 22 of the surgical microscope system 201 includes an image display control unit 41, an in-focus position display control unit 42, and an input unit 43, and the image display control unit 41 to the input unit 43 perform operations similar to the case of FIG. 1.

Such a surgical microscope system 201 has a configuration in which the AF camera unit 211 is provided in place of the contrast AF processing unit 51 of the surgical microscope system 11 shown in FIG. 1.

The AF camera unit 211 is a unit for AF processing for focusing on the target focus position in the front image when the camera image acquisition unit 31 observes the eye of an observation target, that is, when acquires the front image. The AF camera unit 211 includes an AF image acquisition unit 221, an AF camera control unit 222, and an AF processing unit 223.

The AF image acquisition unit 221 captures, for example, an AF camera image, which is an image for AF processing with the patient's eye that is a subject of the front image as a subject, and supplies the AF camera image to the AF processing unit 223. The AF camera image is captured when the front image is acquired.

For example, the AF image acquisition unit 221 includes an AF image sensor that captures an AF camera image, and an AF observation optical system that guides light from the eye that is a subject to the AF image sensor.

Furthermore, for example, an AF objective lens is provided to adjust the focus position of the AF observation optical system when capturing an AF camera image at an end on the eye side that is an observation target in the AF observation optical system. Hereinafter, the focus position of the AF observation optical system, that is, the focus position of the AF objective lens will be particularly referred to as an AF camera focus position. Furthermore, it is assumed that the optical axis direction of the AF objective lens is the Z direction.

Note that part of the AF observation optical system may be shared with the observation optical system of the camera image acquisition unit 31. In such a case, when the AF observation optical system includes a microscope object lens 91, instead of the AF objective lens, an AF focus lens that is not common to the observation optical system may be provided on the AF observation optical system, and the AF camera focus position may be adjusted by the AF focus lens. For example, in a case where the front image is an image of visible light and the AF camera image is infrared light, the AF camera focus position can be adjusted by the AF focus lens without affecting the position at which the illumination light for obtaining the front image is emitted in the Z direction.

The AF camera control unit 222 controls the AF image acquisition unit 221 on the basis of the AF focus position information indicating the target AF camera focus position supplied from the AF processing unit 223, and adjusts the focus position by moving the AF objective lens of the AF image acquisition unit 221.

The AF processing unit 223 calculates the initial in-focus position $d_{init}$ by performing AF processing on the basis of the AF camera image supplied from the AF image acquisition unit 221, and supplies the initial focus position information indicating the initial in-focus position $d_{init}$ to the offset value calculation unit 52.

Furthermore, the AF processing unit 223 sequentially calculates the appropriate AF camera focus position that should be a target during AF processing, and supplies the AF focus position information indicating the AF camera focus position to the AF camera control unit 222.

For example, the AF processing unit 223 performs contrast AF processing and phase difference AF processing as AF processing, but the present technology is not limited to this, and any other processing may be performed. Note that the following description will be continued on an assumption that the AF processing unit 223 performs contrast AF processing as AF processing.

In this case, the AF processing unit 223 extracts the initial in-focus area from the AF camera image. Here, the initial in-focus area is an area that satisfies the extraction condition in the AF camera image, in a similar manner to the case of the first embodiment described above.

Furthermore, the initial in-focus area of the AF camera image may be a predetermined area or an area designated by a user, or an area extracted by the AF processing unit 223 performing image processing.

After extracting the initial in-focus area, the AF processing unit 223 performs contrast AF processing only on the initial in-focus area to calculate the initial in-focus position $d_{init}$.

In the contrast AF processing by the AF processing unit 223, for the AF camera image obtained at each AF camera focus position, the contrast evaluation value is calculated for the initial in-focus area, and the AF camera focus position with the highest contrast evaluation value is detected. The AF camera focus position detected by the contrast AF processing is the AF camera focus position in a state where the area of the eye organ and the like included in the initial in-focus area is in focus.

The AF processing unit 223 sets the camera focus position of the microscope object lens 91 corresponding to the AF camera focus position detected by the contrast AF processing as the initial in-focus position $d_{init}$. It can be said that such an AF processing unit 223 corresponds to the above-described contrast AF processing unit 51 and functions as an initial in-focus position detection unit for detecting the initial in-focus position $d_{init}$ by the contrast AF processing.

Note that the relationship between the focal length of the AF objective lens and the focal length of the microscope object lens 91 is known, for example, by prior calibration and the like. It is possible to convert the focus position of one of the AF objective lens and the microscope object lens 91 into the other focus position.

Furthermore, the AF camera unit 211 and the camera unit 21 may be independent visible light camera units, and the AF camera unit 211 may be sensitive to a specified wavelength, such as an infrared camera, in order to perform AF processing with higher precision.

Moreover, the AF camera unit 211 and the camera unit 21 may be two separate camera systems, or a two-plate camera that is a camera including two image sensors of the image sensor of the camera image acquisition unit 31 and the AF image sensor may constitute the AF camera unit 211 and the camera unit 21.

Furthermore, in the surgical microscope system 201, for example, a configuration including the camera control unit 32, the user I/O 22, the offset value calculation unit 52, and the AF camera unit 211 functions as a control device that performs focus control on the video surgical microscope that acquires the front image and controls image display on the display unit 23.

Besides, for example, in the surgical microscope system 201, depending on the initial in-focus area, parameters regarding focus adjustment may be dynamically changed, such as a time interval parameter, which is a time interval (frequency) for updating the initial in-focus position $d_{init}$, and an adjustment speed parameter, which is the maximum value of an amount of movement (distance) to move the AF camera focus position at one time. With this configuration, a faster and more efficient focus position adjustment can be implemented.

Here, the time interval parameter is a time interval for recalculating (updating) the initial in-focus position $d_{init}$ in the AF camera unit 211.

Furthermore, the adjustment speed parameter is the maximum value that can be taken as an adjustment amount (change amount) of the AF camera focus position that is updated according to an evaluation result when one contrast evaluation, that is, calculation of the contrast evaluation value is performed during contrast AF processing.

Since this maximum value limits the distance to move the AF camera focus position at a time, as a result, the adjustment speed when adjusting the AF camera focus position, that is, the moving speed of the AF camera focus position is limited.

For example, it is assumed that an area including the blood vessel on the sclera of the eye as a subject is extracted as the initial in-focus area on the AF camera image. In this case, since it can be assumed that the position of the blood vessel structure on the sclera does not move largely up and down, that is, in the Z direction, the time interval indicated by the time interval parameter is set long, and the maximum value of the adjustment amount indicated by the adjustment speed parameter is set small.

Furthermore, it is also assumed that, for example, as the initial in-focus area on the AF camera image, an area including an object moving in the depth direction (Z direction) such as a surgical tool is extracted as a subject. In this case, since the surgical tool is likely to be moved frequently, the time interval indicated by the time interval parameter is set short, and the maximum value of the adjustment amount indicated by the adjustment speed parameter is set large.

<Description of Observation Processing>

Figure 11:
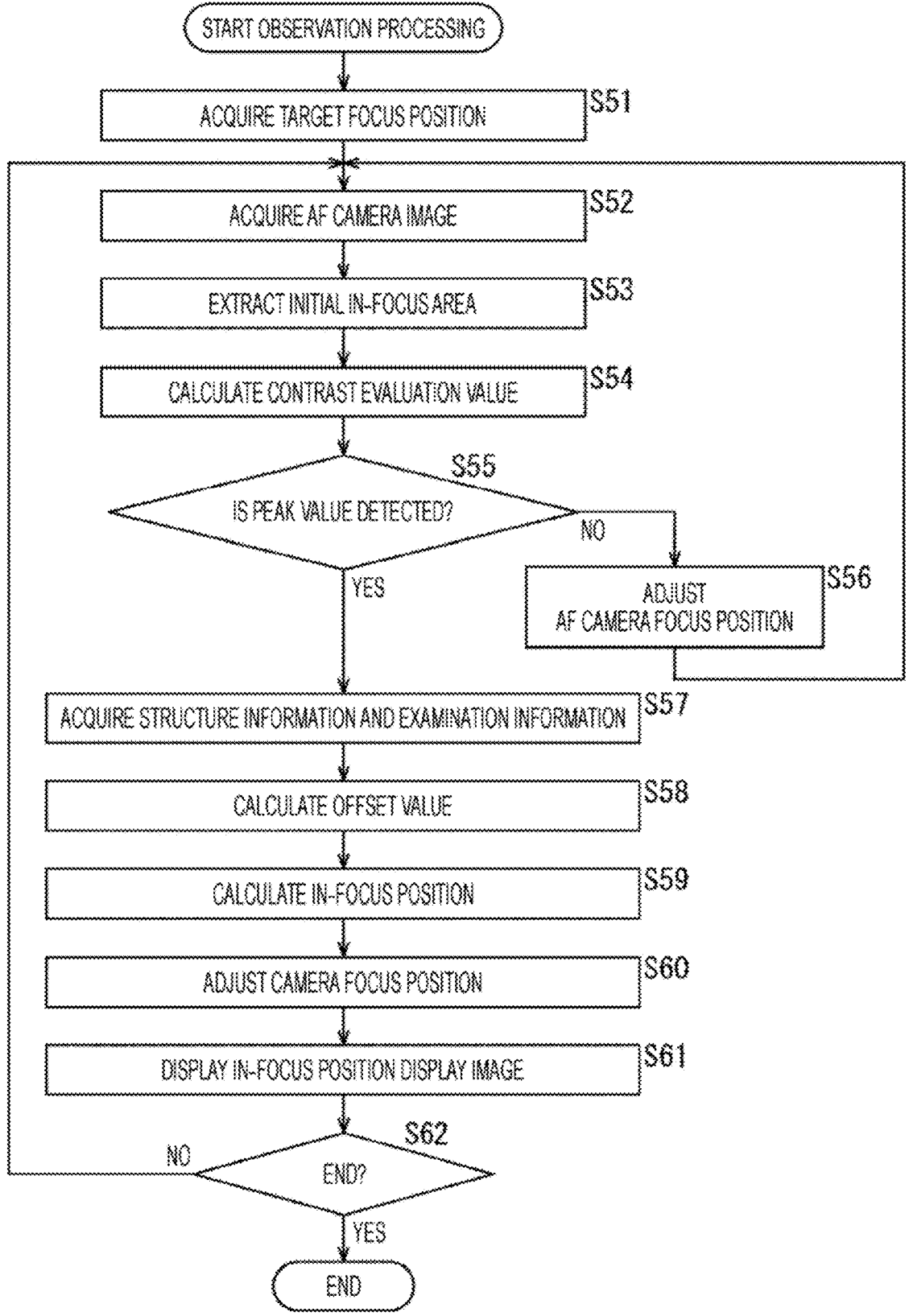
FIG. 11 is a flowchart describing observation processing.

Next, the observation processing performed by the surgical microscope system 201 will be described with reference to the flowchart of FIG. 11.

Figure 9:
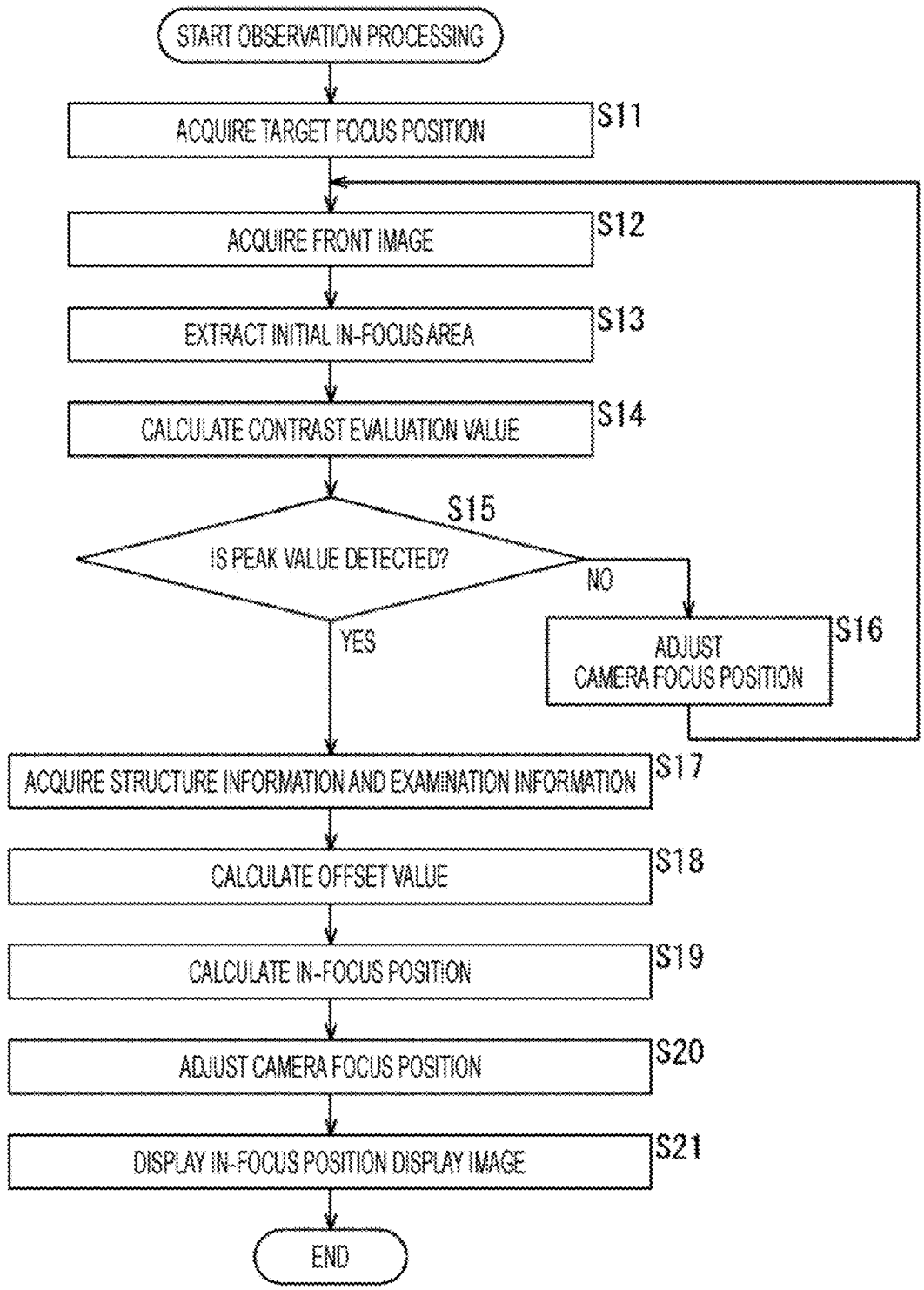
FIG. 9 is a flowchart describing observation processing.

In step S51, the input unit 43 acquires the information indicating the target focus position input by the user in response to the operation on the input unit 43 by the user. The input unit 43 generates input information indicating the target focus position and supplies the input information to the offset value calculation unit 52. In step S51, a process similar to step S11 of FIG. 9 is performed.

In step S52, the AF image acquisition unit 221 acquires the AF camera image of the eye that is an observation target, and supplies the acquired AF camera image to the AF processing unit 223.

Specifically, the AF image sensor captures the AF camera image by receiving and photoelectrically converting light incoming from the eye via the AF observation optical system. Furthermore, the AF image acquisition unit 221 performs various types of image processing such as white balance adjustment on the AF camera image acquired from the AF image sensor to acquire the final AF camera image.

Furthermore, when the acquisition of the AF camera image is started, the camera image acquisition unit 31 starts the acquisition of the front image at the same time, and the display unit 23 displays the display front image.

In step S53, the AF processing unit 223 extracts the initial in-focus area from the AF camera image supplied from the AF image acquisition unit 221. In step S53, a process similar to step S13 of FIG. 9 is performed.

Furthermore, when the AF processing unit 223 extracts the initial in-focus area, the AF processing unit 223 sets the time interval parameter and the adjustment speed parameter according to the initial in-focus area.

Note that what kind of eye organ and the like is included as a subject in the initial in-focus area can be identified, for example, by the position of the initial in-focus area in the AF camera image or the image recognition and the like for the AF camera image. The AF processing unit 223 sets the time interval parameter and the adjustment speed parameter according to the subject included in the initial in-focus area.

In step S54, the AF processing unit 223 calculates the contrast evaluation value for the initial in-focus area extracted from the AF camera image in the process of step S53. In step S54, a process similar to step S14 of FIG. 9 is performed.

Furthermore, the AF processing unit 223 detects the peak value of the contrast evaluation value on the basis of the contrast evaluation value at each AF camera focus position obtained by the process in step S54 performed so far.

In step S55, the AF processing unit 223 determines whether or not the peak value of the contrast evaluation value is detected.

In a case where the peak value of the contrast evaluation value is not detected in step S55, that is, in a case where it is determined that the initial in-focus position $d_{init}$ is not detected, thereafter, the process proceeds to step S56.

In this case, the AF processing unit 223 generates the AF focus position information indicating the AF camera focus position, which is an appropriate destination, on the basis of the contrast evaluation value obtained so far and the set adjustment speed parameter, and supplies the AF focus position information to the AF camera control unit 222.

In step S56, the AF camera control unit 222 controls the AF image acquisition unit 221 on the basis of the AF focus position information supplied from the AF processing unit 223, and adjusts the AF camera focus position.

That is, the AF camera control unit 222 controls the AF image acquisition unit 221 to move the AF object lens in the optical axis direction such that the AF camera focus position of the AF object lens becomes the AF camera focus position indicated by the AF focus position information from the AF processing unit 223

When the AF camera focus position is adjusted, thereafter, the process returns to step S52, and the above processes are repeated until the peak value is detected.

On the other hand, in a case where it is determined in step S55 that the peak value of the contrast evaluation value is detected, since the subject within the initial in-focus area in the AF camera image is focused, thereafter, the process proceeds to step S57.

In this case, the AF processing unit 223 converts the AF camera focus position when the contrast evaluation value that is the detected peak value is obtained into the camera focus position of the microscope object lens 91, and the resultant camera focus position is set as the initial in-focus position $d_{init}$. Then, the AF processing unit 223 supplies the initial focus position information indicating the initial in-focus position $d_{init}$ to the offset value calculation unit 52.

When the initial in-focus position $d_{init}$ is obtained by the above processes, thereafter, the processes of steps S57 to S61 are performed.

When the processes are performed, the camera focus position of the microscope object lens 91 is moved to the in-focus position $d_{focuss}$ and in the front image, a region at the target focus position is in focus, and the display unit 23 displays the in-focus position display image.

Note that the processes of steps S57 to S61 are similar to the processes of steps S17 to S21 of FIG. 9, respectively, and thus descriptions thereof will be omitted.

When the process of step S61 is performed and the in-focus position display image is displayed, thereafter, the process proceeds to step S62.

In step S62, the camera control unit 32 determines whether or not to end the process of acquiring the front image and observing the patient's eye. For example, in a case where the user operates the input unit 43 and the like to give an instruction to end the observation and the like, it is determined to end the process.

In a case where it is determined in step S62 that the process is not yet completed, thereafter, the process returns to step S52, and the above-described processes are repeated.

At this time, for example, after the time indicated by the set time interval parameter has elapsed since the initial in-focus position $d_{init}$ is most recently determined, the processes of next steps S52 to S56 are started. Furthermore, in a case where a new target focus position is input by the user during the process, that is, in a case where the target focus position is updated, the process of step S51 is performed, and thereafter, the processes of step S52 and subsequent steps are performed.

On the other hand, in a case where it is determined in step S62 that the process is to be ended, each part of the surgical microscope system 201 stops the operation for observing the patient's eye and the observation processing ends.

As described above, the surgical microscope system 201 obtains the initial in-focus position $d_{init}$ by contrast AF processing on the basis of the AF camera image obtained by the AF image acquisition unit 221 for AF processing different from the camera image acquisition unit 31. Then, the surgical microscope system 201 calculates the final in-focus position $d_{focuss}$ from the initial in-focus position $d_{init}$, and moves the camera focus position of the microscope object lens 91 to the region at the target focus position.

With this operation, even in a case where the target focus position is a transparent body, the target focus position can be focused at high speed and with high precision. That is, it is possible to focus on the desired position of the subject.

In particular, in the surgical microscope system 201, the initial in-focus position $d_{init}$ is determined by the AF camera unit 211 that does not affect the focus position of the front image, that is, the focus position of the microscope object lens 91. Therefore, the in-focus position $d_{focuss}$ of the microscope object lens 91 can be determined with the subject such as a transparent body at the target focus position always in focus in the front image. That is, the camera focus position of the microscope object lens 91 can be moved to an appropriate position by following the movement of the subject to be focused in the Z direction.

As described above, with the present technology, even in a case where the region of the subject that is an observation target to be focused is a transparent body, the region can be focused, and it is possible to provide a clear front image without a blur, that is, a clear surgical operation image.

If such a clear surgical operation image is obtained, operators and the like can reduce the number of times to operate the surgical microscope system, particularly the video surgical microscope, thereby improving the efficiency of the surgical operation and shortening the time required for the surgical operation.

Furthermore, since the in-focus position display image showing the in-focus position is displayed, the user can intuitively determine the focus position of the microscope object lens 91, that is, the position where focus is achieved.

Moreover, in the second embodiment, without moving the camera focus position of the microscope object lens 91 more than necessary, it is possible to maintain a focused state on the subject such as a transparent body at the target focus position by continuous AF, and to follow the movement of the target subject at high speed.

<Configuration Example of Computer>

In that connection, a series of processes described above can be performed by hardware, or can be performed by software. In a case where the series of processes is performed by software, a program constituting the software is installed in a computer. Here, the computer includes a computer embedded in dedicated hardware, and for example, a general-purpose personal computer and the like that can execute various functions by installing various programs.

Figure 12:
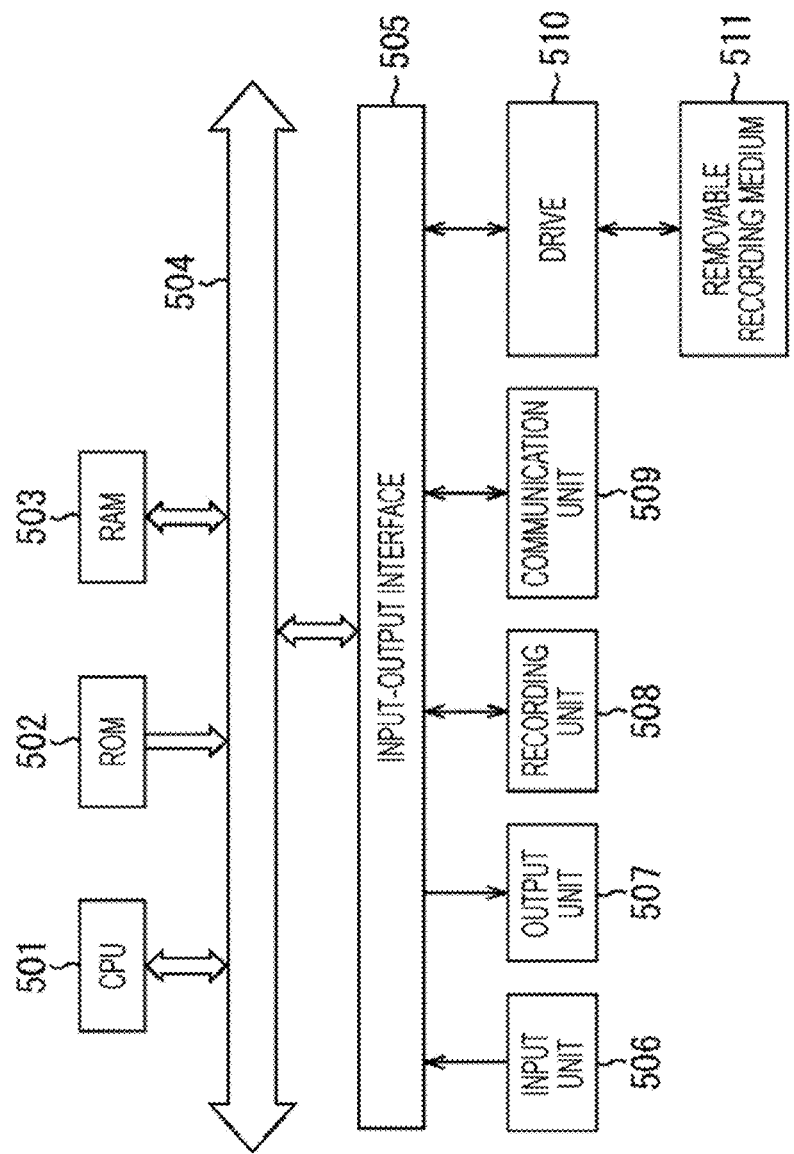
FIG. 12 is a diagram showing a configuration example of a computer.

FIG. 12 is a block diagram showing a configuration example of hardware of a computer that performs the series of processes described above by the program.

In the computer, a central processing unit (CPU) 501, a read only memory (ROM) 502, and a random access memory (RAM) 503 are connected to each other by a bus 504.

An input-output interface 505 is further connected to the bus 504. An input unit 506, an output unit 507, a recording unit 508, a communication unit 509, and a drive 510 are connected to the input-output interface 505.

The input unit 506 includes a keyboard, a mouse, a microphone, an image capturing element, and the like. The output unit 507 includes a display, a speaker, and the like. The recording unit 508 includes a hard disk, a non-volatile memory, and the like. The communication unit 509 includes a network interface and the like. The drive 510 drives a removable recording medium 511 such as a magnetic disk, an optical disk, a magneto-optical disk, a semiconductor memory, and the like.

In the computer configured as described above, the CPU 501 loads, for example, a program recorded in the recording unit 508 into the RAM 503 via the input-output interface 505 and the bus 504 and executes the program, whereby the above-described series of processes is performed.

The program executed by the computer (CPU 501) can be provided, for example, by being recorded in the removable recording medium 511 such as a package medium. Furthermore, the program can be provided via a wired or wireless transmission medium such as a local area network, the Internet, or digital satellite broadcasting.

In the computer, the program can be installed in the recording unit 508 via the input-output interface 505 by mounting the removable recording medium 511 in the drive 510. Furthermore, the program can be received by the communication unit 509 via a wired or wireless transmission medium and installed in the recording unit 508. Besides, the program can be installed in advance in the ROM 502 or the recording unit 508.

Note that the program to be executed by the computer may be a program in which processing is performed on a time-series basis in the order described in this specification, or may be a program in which processing is performed in parallel or at necessary timing such as when a call is made.

Furthermore, embodiments of the present technology are not limited to the embodiments described above, and various modifications may be made without departing from the spirit of the present technology.

For example, the present technology can have a configuration of cloud computing in which one function is shared and processed together by a plurality of devices via a network.

Furthermore, each step described in the above flowchart can be executed by one device or shared by a plurality of devices.

Moreover, in a case where one step includes a plurality of processes, the plurality of processes included in the one step can be executed by one device or shared by a plurality of devices.

Moreover, the present technology can also have the following configurations.

(1)

A control device including:

an initial in-focus position detection unit configured to detect a focus position when focusing on a predetermined subject included in an observation image of an eye of a patient that is a surgical operation target as an initial in-focus position; and a calculation unit configured to determine an offset value indicating a distance between a target eye organ that is inside a corneal endothelium of the eye and the initial in-focus position on the basis of information regarding structure of an eyeball, and to calculate an in-focus position that is a focus position focused on the target eye organ on the basis of the offset value and the initial in-focus position.

(2)

The control device according to (1), further including a control unit configured to adjust the focus position to become the in-focus position calculated by the calculation unit.

(3)

The control device according to (1) or (2), in which the initial in-focus position detection unit extracts an initial in-focus area including the predetermined subject from the observation image, and detects the initial in-focus position on the basis of the initial in-focus area.

(4)

The control device according to (3), in which the initial in-focus position detection unit detects the initial in-focus position by performing contrast AF processing on the initial in-focus area.

(5)

The control device according to (1) or (2), in which the initial in-focus position detection unit detects the initial in-focus position on the basis of an AF image of the eye of the patient different from the observation image.

(6)

The control device according to (5), in which the initial in-focus position detection unit extracts an initial in-focus area including the predetermined subject from the AF image, and detects the initial in-focus position on the basis of the initial in-focus area.

(7)

The control device according to (6), in which the initial in-focus position detection unit detects the initial in-focus position by performing contrast AF processing on the initial in-focus area.

(8)

The control device according to any one of (1) to (7), in which the calculation unit corrects the offset value on the basis of information peculiar to the patient.

(9)

The control device according to any one of (1) to (8), in which the information regarding the structure of the eyeball includes structure information indicating a positional relationship of each eye organ of the eyeball.

(10)

The control device according to any one of (1) to (8), in which the information regarding the structure of the eyeball includes a tomographic image of the eye of the patient obtained before a surgical operation.

(11)

The control device according to any one of (1) to (8), in which the information regarding the structure of the eyeball includes a tomographic image of the eye of the patient obtained during a surgical operation.

(12)

The control device according to any one of (1) to (11), further including an in-focus position display control unit configured to display an in-focus position display image indicating the in-focus position in a cross section of the eyeball.

(13)

The control device according to (12), in which the calculation unit calculates the in-focus position with an eye organ at a designated position on the in-focus position display image as the target eye organ.

(14)

The control device according to (12) or (13), further including an image display control unit configured to display the observation image, in which the observation image and the in-focus position display image are displayed side by side.

(15)

The control device according to any one of (1) to (14), in which the target eye organ includes a transparent body.

(16)

The control device according to any one of (1) to (15), in which the predetermined subject includes an eye organ of the eye or a surgical tool.

(17)

A control method including, by a control device:

detecting a focus position when a predetermined subject included in an observation image of an eye of a patient that is a surgical operation target is focused as an initial in-focus position; and determining an offset value indicating a distance between a target eye organ inside a corneal endothelium of the eye and the initial in-focus position on the basis of information regarding structure of an eyeball, and calculating an in-focus position that is a focus position focused on the target eye organ on the basis of the offset value and the initial in-focus position.

(18)

A surgical microscope system including:

an image acquisition unit configured to acquire an observation image of an eye of a patient that is a surgical operation target;

an initial in-focus position detection unit configured to detect a focus position of the image acquisition unit when a predetermined subject included in the observation image is focused as an initial in-focus position; and a calculation unit configured to determine an offset value indicating a distance between a target eye organ inside a corneal endothelium of the eye and the initial in-focus position on the basis of information regarding structure of an eyeball, and to calculate an in-focus position that is a focus position of the image acquisition unit focused on the target eye organ on the basis of the offset value and the initial in-focus position.

REFERENCE SIGNS LIST

11 Surgical microscope system
31 Camera image acquisition unit
32 Camera control unit
41 Image display control unit
42 In-focus position display control unit
43 Input unit
51 Contrast AF processing unit
52 Offset value calculation unit
201 Surgical microscope system
221 AF image acquisition unit
222 AF camera control unit
223 AF processing unit

The invention claimed is:

1. A control device comprising:
  circuitry configured to:
    detect, for focusing on a predetermined subject included in an observation image of an eye of a patient that is a surgical operation target, an initial in-focus position on a basis of an autofocus image of the eye of the patient off-center from the observation image;
    determine an offset value indicating a distance between a target eye organ that is inside a corneal endothelium of the eye and the initial in-focus position on a basis of information regarding structure of an eyeball; and
    calculate an in-focus position for a center of the observation image that is a focus position focused on the target eye organ on a basis of the offset value and the initial in-focus position.

2. The control device according to claim 1,
wherein the circuitry is configured to adjust the focus position to become the in-focus position calculated.

3. The control device according to claim 1, wherein
the circuitry is configured to extract an initial in-focus area including the predetermined subject from the observation image, and detect the initial in-focus position on a basis of the initial in-focus area.

4. The control device according to claim 3, wherein
the circuitry is configured to detect the initial in-focus position by performing contrast autofocus processing on the initial in-focus area.

5. The control device according to claim 1, wherein
the circuitry is configured to
extract an initial in-focus area including the predetermined subject from the autofocus image, and
detect the initial in-focus position on a basis of the initial in-focus area.

6. The control device according to claim 5, wherein
the circuitry is configured to detect the initial in-focus position by performing contrast autofocus processing on the initial in-focus area.

7. The control device according to claim 1, wherein
the circuitry is configured to correct the offset value on a basis of information of the eye of the patient obtained from an external diagnostic device.

8. The control device according to claim 1, wherein
the information regarding the structure of the eyeball includes structure information indicating a positional relationship of each eye organ of the eyeball.

9. The control device according to claim 7, wherein
the external diagnostic device provides a tomographic image of the eye of the patient obtained before a surgical operation.

10. The control device according to claim 7, wherein
the external diagnostic device provides a tomographic image of the eye of the patient obtained during a surgical operation.

11. The control device according to claim 1,
wherein the circuitry is configured to output an in-focus position display image indicating the in-focus position in a cross section of the eyeball to a display.

12. The control device according to claim 11, wherein the circuitry is configured to calculate the in-focus position with an eye organ at a designated position on the in-focus position display image as the target eye organ.

13. The control device according to claim 11, wherein the circuitry is configured to control display the observation image, wherein such that the observation image and the in-focus position display image are displayed side by side on the display.

14. The control device according to claim 1, wherein the target eye organ includes a transparent body.

15. The control device according to claim 1, wherein the predetermined subject includes an eye organ of the eye or a surgical tool.

16. A control method comprising, by a control device:
detecting, for focusing on a predetermined subject included in an observation image of an eye of a patient that is a surgical operation target, an initial in-focus position on a basis of an autofocus image of the eye of the patient off-center from the observation image; and
determining an offset value indicating a distance between a target eye organ inside a corneal endothelium of the eye and the initial in-focus position on a basis of information regarding structure of an eyeball, and calculating an in-focus position calculate an in-focus position for a center of the observation image that is a focus position focused on the target eye organ on a basis of the offset value and the initial in-focus position.

17. A surgical microscope system comprising:
an image sensor configured to acquire an observation image of an eye of a patient that is a surgical operation target; and
circuitry configured to:
detect, for focusing on a predetermined subject included in an observation image of an eye of a patient that is a surgical operation target, an initial in-focus position on a basis of an autofocus image of the eye of the patient off-center from the observation image;
determine an offset value indicating a distance between a target eye organ that is inside a corneal endothelium of the eye and the initial in-focus position on a basis of information regarding structure of an eyeball; and
calculate an in-focus position for a center of the observation image that is a focus position focused on the target eye organ on a basis of the offset value and the initial in-focus position.

18. The control device according to claim 1, wherein the autofocus image of the eye of the patient includes an area adjacent to a center of the observation image.

19. The control device according to claim 18, wherein the area adjacent to a center of the observation image is annular.

20. The control device according to claim 1, wherein the autofocus image of the eye of the patient includes a surgical tool.

* * * * *